United States Patent
Hettrick et al.

(10) Patent No.: US 10,231,784 B2
(45) Date of Patent: Mar. 19, 2019

(54) METHODS AND SYSTEMS FOR OPTIMIZING PERIVASCULAR NEUROMODULATION THERAPY USING COMPUTATIONAL FLUID DYNAMICS

(71) Applicant: Medtronic Ardian Luxembourg S.a.r.l., Luxembourg (LU)

(72) Inventors: Douglas Hettrick, Andover, MN (US); Julie Trudel, Santa Rosa, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 306 days.

(21) Appl. No.: 15/337,742

(22) Filed: Oct. 28, 2016

(65) Prior Publication Data

US 2018/0116723 A1    May 3, 2018

(51) Int. Cl.
 *A61B 34/10*      (2016.01)
 *A61B 5/022*      (2006.01)
    (Continued)

(52) U.S. Cl.
 CPC .............. *A61B 34/10* (2016.02); *A61B 5/022* (2013.01); *A61B 5/026* (2013.01); *A61B 5/02007* (2013.01); *A61B 5/0215* (2013.01); *A61B 5/055* (2013.01); *A61B 5/0538* (2013.01); *A61B 5/6851* (2013.01); *A61B 6/032* (2013.01); *A61B 6/504* (2013.01); *A61B 8/06* (2013.01);
    (Continued)

(58) Field of Classification Search
 CPC .............. A61B 34/10; A61B 2034/101; A61B 2034/107
 See application file for complete search history.

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| EP | 1169976 | 1/2002 |
| EP | 2316371 A1 | 5/2011 |

(Continued)

OTHER PUBLICATIONS

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

(Continued)

*Primary Examiner* — Ronald Hupczey, Jr.

(57) ABSTRACT

Methods and systems for optimizing perivascular neuromodulation therapy using computational fluid dynamics. Digital data regarding three-dimensional imaging of a target blood vessel and corresponding hemodynamic data are inputs to generating a computational fluid dynamics (CFD) model. The CFD model enables identification of one or more regions of the vessel suitable for neuromodulation therapy and/or identifying one or more regions of the vessel to avoid during such therapy. A system of the present technology can include a neuromodulation catheter, a computing device that can generate and analyze the CFD model, and a user interface for displaying the vessel with indicia for target regions and/or avoidance regions.

28 Claims, 16 Drawing Sheets

(51) Int. Cl.

| | | |
|---|---|---|
| *A61B 5/026* | (2006.01) | |
| *A61B 5/053* | (2006.01) | |
| *A61B 5/055* | (2006.01) | |
| *A61B 5/00* | (2006.01) | |
| *A61B 6/03* | (2006.01) | |
| *A61B 6/00* | (2006.01) | |
| *A61B 8/06* | (2006.01) | |
| *A61B 8/08* | (2006.01) | |
| *A61B 18/02* | (2006.01) | |
| *A61B 18/14* | (2006.01) | |
| *A61N 1/05* | (2006.01) | |
| *A61N 1/36* | (2006.01) | |
| *A61B 5/02* | (2006.01) | |
| *A61B 5/0215* | (2006.01) | |
| *A61B 18/00* | (2006.01) | |
| *A61N 7/00* | (2006.01) | |
| *A61B 34/20* | (2016.01) | |
| *A61B 34/00* | (2016.01) | |

(52) U.S. Cl.
CPC .............. *A61B 8/488* (2013.01); *A61B 18/02* (2013.01); *A61B 18/1492* (2013.01); *A61N 1/0551* (2013.01); *A61N 1/36117* (2013.01); *A61B 2018/0022* (2013.01); *A61B 2018/00404* (2013.01); *A61B 2018/00434* (2013.01); *A61B 2018/00511* (2013.01); *A61B 2018/00577* (2013.01); *A61B 2018/00863* (2013.01); *A61B 2018/00875* (2013.01); *A61B 2018/0212* (2013.01); *A61B 2018/1467* (2013.01); *A61B 2018/1475* (2013.01); *A61B 2034/105* (2016.02); *A61B 2034/107* (2016.02); *A61B 2034/2051* (2016.02); *A61B 2034/254* (2016.02); *A61N 7/00* (2013.01)

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,301,683 A | 4/1994 | Durkan |
| 5,358,514 A | 10/1994 | Schulman et al. |
| 5,368,591 A | 11/1994 | Lennox et al. |
| 5,423,744 A | 6/1995 | Gencheff et al. |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,860,974 A | 1/1999 | Abele |
| 5,865,787 A | 2/1999 | Shapland et al. |
| 5,893,885 A | 4/1999 | Webster et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Eggers et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto |
| 6,939,346 B2 | 9/2005 | Kannenberg et al. |
| 6,949,097 B2 | 9/2005 | Stewart et al. |
| 7,149,574 B2 | 12/2006 | Yun et al. |
| 7,160,296 B2 | 1/2007 | Pearson et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,702,619 B2 | 4/2014 | Wang |
| 8,768,470 B2 | 7/2014 | Deem et al. |
| 8,909,316 B2 | 12/2014 | Ng |
| 8,977,359 B2 | 3/2015 | Rossing |
| 9,002,446 B2 | 4/2015 | Wenzel et al. |
| 9,014,809 B2 | 4/2015 | Wenzel |
| 9,014,821 B2 | 4/2015 | Wang |
| 9,022,948 B2 | 5/2015 | Wang |
| 9,043,191 B2 | 5/2015 | Grady et al. |
| 9,119,600 B2 | 9/2015 | Richardson et al. |
| 9,168,094 B2 | 10/2015 | Lee et al. |
| 9,179,973 B2 | 11/2015 | Nabutovsky et al. |
| 9,186,212 B2 | 11/2015 | Nabutovsky et al. |
| 9,295,842 B2 | 3/2016 | Ghaffari et al. |
| 9,314,300 B2 | 4/2016 | Nabutovsky et al. |
| 9,375,154 B2 | 6/2016 | Wang |
| 9,427,283 B2 | 8/2016 | Nabutovsky et al. |
| 9,427,579 B2 | 8/2016 | Fain et al. |
| 9,554,850 B2 | 1/2017 | Lee et al. |
| 9,579,030 B2 | 2/2017 | Scheuermann et al. |
| 2002/0139379 A1 | 10/2002 | Edwards et al. |
| 2002/0165532 A1 | 11/2002 | Hill et al. |

(56) References Cited

U.S. PATENT DOCUMENTS

| | | |
|---|---|---|
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0215186 A1 | 10/2004 | Cornelius et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2006/0085054 A1 | 4/2006 | Zikorus et al. |
| 2006/0095029 A1 | 5/2006 | Young et al. |
| 2006/0206150 A1 | 9/2006 | Demarais et al. |
| 2006/0271111 A1 | 11/2006 | Demarais et al. |
| 2007/0129720 A1 | 6/2007 | Demarais et al. |
| 2007/0265687 A1 | 11/2007 | Deem et al. |
| 2008/0319513 A1 | 12/2008 | Pu et al. |
| 2009/0036948 A1 | 2/2009 | Levin et al. |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2011/0112400 A1 | 5/2011 | Emery et al. |
| 2011/0270120 A1 | 11/2011 | McFarlin et al. |
| 2011/0306851 A1 | 12/2011 | Wang |
| 2012/0029504 A1 | 2/2012 | Afonso et al. |
| 2012/0123400 A1 | 5/2012 | Francischelli et al. |
| 2012/0130289 A1 | 5/2012 | Demarais et al. |
| 2012/0130345 A1 | 5/2012 | Levin et al. |
| 2012/0143097 A1 | 6/2012 | Pike, Jr. |
| 2012/0172837 A1 | 7/2012 | Demarais et al. |
| 2012/0172870 A1 | 7/2012 | Jenson et al. |
| 2012/0191079 A1 | 7/2012 | Moll et al. |
| 2012/0296232 A1 | 11/2012 | Ng |
| 2012/0296329 A1 | 11/2012 | Ng |
| 2013/0172878 A1 | 7/2013 | Smith |
| 2013/0218029 A1 | 8/2013 | Cholette et al. |
| 2013/0274614 A1 | 10/2013 | Shimada et al. |
| 2013/0282001 A1 | 10/2013 | Hezi-Yamit et al. |
| 2014/0005535 A1 | 1/2014 | Edic et al. |
| 2014/0012133 A1 | 1/2014 | Sverdlik et al. |
| 2014/0066803 A1 | 3/2014 | Choi |
| 2014/0073903 A1 | 3/2014 | Weber et al. |
| 2014/0074089 A1 | 3/2014 | Nishii |
| 2014/0128865 A1 | 5/2014 | Gross |
| 2014/0213873 A1 | 7/2014 | Wang |
| 2014/0221805 A1 | 8/2014 | Wang |
| 2014/0236011 A1* | 8/2014 | Fan .................. A61B 5/6876 600/440 |
| 2014/0236137 A1 | 8/2014 | Tran et al. |
| 2014/0236138 A1 | 8/2014 | Tran et al. |
| 2014/0246465 A1 | 9/2014 | Peterson et al. |
| 2014/0249524 A1 | 9/2014 | Kocur |
| 2014/0266235 A1 | 9/2014 | Mathur |
| 2014/0275924 A1 | 9/2014 | Min et al. |
| 2014/0276124 A1 | 9/2014 | Cholette et al. |
| 2014/0276733 A1 | 9/2014 | VanScoy et al. |
| 2014/0276755 A1 | 9/2014 | Cao et al. |
| 2014/0276762 A1 | 9/2014 | Parsonage |
| 2014/0276766 A1 | 9/2014 | Brotz et al. |
| 2014/0276767 A1 | 9/2014 | Brotz et al. |
| 2014/0276773 A1 | 9/2014 | Brotz et al. |
| 2014/0316400 A1 | 10/2014 | Blix et al. |
| 2014/0316496 A1 | 10/2014 | Masson et al. |
| 2014/0330267 A1 | 11/2014 | Harrington |
| 2014/0336637 A1 | 11/2014 | Agrawal et al. |
| 2015/0005764 A1 | 1/2015 | Hanson et al. |
| 2015/0018656 A1 | 1/2015 | Min et al. |
| 2015/0025524 A1 | 1/2015 | Nabutovsky |
| 2015/0112329 A1 | 4/2015 | Ng |
| 2015/0119674 A1 | 4/2015 | Fischell et al. |
| 2015/0173673 A1 | 6/2015 | Toth et al. |
| 2015/0201997 A1 | 7/2015 | Osypka |
| 2015/0216590 A1 | 8/2015 | Wang et al. |
| 2015/0223877 A1 | 8/2015 | Behar et al. |
| 2015/0224326 A1 | 8/2015 | Toth et al. |
| 2015/0242588 A1* | 8/2015 | Audigier .................. A61B 34/10 606/41 |
| 2015/0289929 A1 | 10/2015 | Toth et al. |
| 2015/0366609 A1 | 12/2015 | Richardson et al. |
| 2016/0000345 A1 | 1/2016 | Kobayashi et al. |
| 2016/0029960 A1 | 2/2016 | Toth et al. |
| 2016/0038028 A1 | 2/2016 | Buelna et al. |
| 2016/0081744 A1 | 3/2016 | Wang |
| 2016/0106498 A1 | 4/2016 | Highsmith et al. |
| 2016/0184010 A1 | 6/2016 | Nabutovsky et al. |
| 2016/0213262 A1 | 7/2016 | Ghaffari et al. |
| 2016/0213424 A1 | 7/2016 | Ghaffari et al. |
| 2016/0324572 A1 | 11/2016 | Gross et al. |
| 2016/0331451 A1 | 11/2016 | Nabutovsky et al. |
| 2016/0331453 A1 | 11/2016 | Fain et al. |
| 2016/0374568 A1 | 12/2016 | Wang |

FOREIGN PATENT DOCUMENTS

| | | |
|---|---|---|
| EP | 2594193 A2 | 5/2013 |
| EP | 2613704 A2 | 7/2013 |
| EP | 2709517 A1 | 3/2014 |
| EP | 2747691 A1 | 7/2014 |
| EP | 2797535 A1 | 11/2014 |
| EP | 2852339 | 4/2015 |
| EP | 2866645 | 5/2015 |
| EP | 2887900 | 7/2015 |
| EP | 2907464 | 8/2015 |
| EP | 2914334 | 9/2015 |
| EP | 2967383 | 1/2016 |
| EP | 2978372 | 2/2016 |
| EP | 3011899 | 4/2016 |
| EP | 3028628 | 6/2016 |
| EP | 3089686 | 11/2016 |
| JP | H08504531 | 5/1996 |
| JP | H1071037 | 3/1998 |
| JP | 2001518808 | 10/2001 |
| JP | 2005278739 | 10/2005 |
| JP | 2008515544 A | 5/2008 |
| JP | 2009539565 A | 11/2009 |
| JP | 2010162163 | 7/2010 |
| JP | 2010533513 | 10/2010 |
| JP | 2011505929 | 3/2011 |
| JP | 2015073691 | 4/2015 |
| WO | WO-2014091328 A1 | 7/1989 |
| WO | WO-1994007446 A1 | 4/1994 |
| WO | WO-1995025472 A1 | 9/1995 |
| WO | WO-1995031142 A1 | 11/1995 |
| WO | WO-1997036548 A1 | 10/1997 |
| WO | WO-1998042403 A1 | 10/1998 |
| WO | WO-1999000060 A1 | 1/1999 |
| WO | WO-2001022897 A1 | 4/2001 |
| WO | WO-2001070114 A1 | 9/2001 |
| WO | WO-2003022167 | 3/2003 |
| WO | WO-2003082080 | 10/2003 |
| WO | WO-2005030072 A1 | 4/2005 |
| WO | WO-2005041748 A2 | 5/2005 |
| WO | WO-2005110528 A1 | 11/2005 |
| WO | WO-2006041881 A2 | 4/2006 |
| WO | WO-2006105121 A2 | 10/2006 |
| WO | WO-2007008954 A2 | 1/2007 |
| WO | WO-2007078997 A2 | 7/2007 |
| WO | WO-2008003058 | 1/2008 |
| WO | WO-2008049084 A2 | 4/2008 |
| WO | WO-2010078175 A1 | 7/2010 |
| WO | WO-2011089935 | 7/2011 |
| WO | WO-2012033974 A2 | 3/2012 |
| WO | 2012061159 | 5/2012 |
| WO | WO-2012068471 A1 | 5/2012 |
| WO | WO-2012158864 A1 | 11/2012 |

(56) References Cited

FOREIGN PATENT DOCUMENTS

| WO | WO-2013030738 A1 | 3/2013 |
|---|---|---|
| WO | WO-2013030743 A1 | 3/2013 |
| WO | WO-2013074813 | 5/2013 |
| WO | WO-2013101485 | 7/2013 |
| WO | WO-2013112844 A2 | 8/2013 |
| WO | WO-2014012282 A1 | 1/2014 |
| WO | WO-2014029355 A1 | 2/2014 |
| WO | WO-2014059165 A2 | 4/2014 |
| WO | WO-2014068577 A2 | 5/2014 |
| WO | WO-2014068606 | 5/2014 |
| WO | WO-2014091401 A2 | 6/2014 |
| WO | WO-2014149550 A2 | 9/2014 |
| WO | WO-2014149552 A1 | 9/2014 |
| WO | WO-2014149553 A1 | 9/2014 |
| WO | WO-2014149690 A2 | 9/2014 |
| WO | WO-2014150425 A1 | 9/2014 |
| WO | WO-2014150432 A1 | 9/2014 |
| WO | WO-2014150441 A2 | 9/2014 |
| WO | WO-2014150455 A1 | 9/2014 |
| WO | WO-2014158708 A1 | 10/2014 |
| WO | WO-2014158713 A1 | 10/2014 |
| WO | WO-2014163990 A1 | 10/2014 |
| WO | WO-2014179768 A1 | 11/2014 |
| WO | WO-2014182946 A2 | 11/2014 |
| WO | 2016100720 | 6/2016 |

OTHER PUBLICATIONS

Avitall et al., "The creation of linear contiguous lesions in the atria with an expandable loop catheter," Journal of the American College of Cardiology, 1999; 33; pp. 972-984.

Beale et al., "Minimally Invasive Treatment for Varicose Veins: A Review of Endovenous Laser Treatment and Radiofrequency Ablation". Lower Extremity Wounds 3(4), 2004, 10 pages.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

ClinicalTrials.gov, Renal Denervation in Patients with uncontrolled Hypertension in Chinese (2011), 6pages. www.clinicaltrials.gov/ct2/show/NCT01390831.

Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.

Excerpt of Operator's Manual of Boston Scientific's EPT-1000 XP Cardiac Ablation Controller & Accessories, Version of Apr. 2003, (6 pages).

Excerpt of Operator's Manual of Boston Scientific's Maestro 30000 Cardiac Ablation System, Version of Oct. 17, 2005 , (4 pages).

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Kandarpa, Krishna et al., "Handbook of Interventional Radiologic Procedures", Third Edition, pp. 194-210 (2002).

Mount Sinai School of Medicine clinical trial for Impact of Renal Sympathetic Denervation of Chronic Hypertension, Mar. 2013, 11 pages. http://clinicaltrials.gov/ct2/show/NCT01628198.

Opposition to European Patent No. 2465470, Granted Oct. 28, 2015, Date of Opposition Jul. 27, 2016, 34 pages.

Opposition to European Patent No. EP1802370, Granted Jan. 5, 2011, Date of Opposition Oct. 5, 2011, 20 pages.

Opposition to European Patent No. EP2037840, Granted Dec. 7, 2011, Date of Opposition Sep. 7, 2012, 25 pages.

Opposition to European Patent No. EP2092957, Granted Jan. 5, 2011, Date of Opposition Oct. 5, 2011, 26 pages.

Oz, Mehmet, Pressure Relief, TIME, Jan. 9, 2012, 2 pages. <www.time.come/time/printout/0,8816,2103278,00.html/>.

Papademetriou, Vasilios, Renal Sympathetic Denervation for the Treatment of Difficult-to-Control or Resistant Hypertension, Int. Journal of Hypertension, 2011, 8 pages.

Pieper, et al., "Design and Implementation of a New Computerized System for Intraoperative Cardiac Mapping" Journal of Applied Physiology, 1991, vol. 71 (4), pp. 1529-1539.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Purerfellner, Helmut et al., Pulmonary Vein Stenosis Following Catheter Ablation of Atrial Fibrillation, Curr. Opin. Cardio. 20 :484-490, 2005.

Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.

Schneider, Peter A., "Endovascular Skills—Guidewire and Catheter Skills for Endovascular Surgery," Second Edition Revised and Expanded, 10 pages, (2003).

ThermoCool Irrigated Catheter and Integrated Ablation System, Biosense Webster (2006), 6 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.

Wittkampf et al., "Control of radiofrequency lesion size by power regulation," Journal of the American Heart Associate, 1989, 80: pp. 962-968.

Zheng et al., "Comparison of the temperature profile and pathological effect at unipolar, bipolar and phased radiofrequency current configurations," Journal of Interventional Cardiac Electrophysiology, 2001, pp. 401-410.

U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.

"2011 Edison Award Winners." Edison Awards: Honoring Innovations & Innovators, 2011, 6 pages, <http://www.edisonawards.com/BestNewProduct_2011.php>.

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.

"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.

"Does renal denervation represent a new treatment option for resistant hypertension?" Interventional News, Aug. 3, 2010, 2 pages. <http://www.cxvascular.com/in-latest-news/interventional-

(56) References Cited

OTHER PUBLICATIONS news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing The Medical Device Industry." Fast Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." Am. J. Roentgenol,174: 1592-1594 (2000).
Han, Y.-M, et al., "Renal artery embolization with diluted hot contrast medium: An experimental study." J Vasc Interv Radiol, 12: 862-868 (2001).
Hansen, J. M., et al. "The transplanted human kidney does not achieve functional reinnervation." Clin. Sci, 87: 13-19 (1994).
Hendee, W. R. et al. "Use of Animals in Biomedical Research: The Challenge and Response." American Medical Association White Paper (1988) 39 pages.
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S. J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D. L., et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages,

(56) References Cited

OTHER PUBLICATIONS

<http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Stella, A., et al., "Effects of reversible renal denervation on haemodynamic and excretory functions on the ipsilateral and contralateral kidney in the cat." Hypertension, 4:181-188 (1986).

Stouffer, G. A. et al., "Catheter-based renal denervation in the treatment of resistant hypertension." Journal of Molecular and Cellular Cardiology, vol. 62, 2013, 6 pages.

Swartz, J. F., et al., "Radiofrequency endocardial catheter ablation of accessory atrioventricular pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Weinstock, M., et al., "Renal denervation prevents sodium retention and hypertension in salt sensitive rabbits with genetic baroreflex impairment." Clinical Science, 90:287-293 (1996).

Wilcox, Josiah N., Scientific Basis Behind Renal Denervation for the Control of Hypertension, ICI 2012, Dec. 5-6, 2012. 38 pages.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen, "The St. Jude Renal Denervation System Technology and Clinical Review." The University of Adelaide Australia, 2012, 24 pages.

Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

Miller, Reed, "Finding a Future for Renal Denervation With Better Controlled Trials." Pharma & Medtech Business Intelligence, Article # 01141006003, Oct. 6, 2014, 4 pages.

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Doumas, Michael et al., "Renal Nerve Ablation for Resistant Hypertension: The Dust Has Not Yet Settled." The Journal of Clinical Hypertension. 2014; vol. 16, No. 6, 2 pages.

Messerli, Franz H. et al. "Renal Denervation for Resistant Hypertension: Dead or Alive?" Healio: Cardiology today's Intervention, May/Jun. 2014, 2 pages.

Böhm M, Mahfoud F, Ukena C, Hoppe UC, Narkiewicz K, Negoita M, Ruilope L, Schlaich MP, Schmieder RE, Whitbourn R, Williams B, Zeymer U, Zirlik A, Mancia G; "GSR investigators First report of the Global Symplicity Registry on the effect of renal artery denervation in patients with uncontrolled hypertension." Hypertension. Apr. 2015;65(4):766-74.

Soulis JV1, Fytanidis DK1, Seralidou KV1, Giannoglou GD2, "Wall shear stress oscillation and its gradient in the normal left coronary artery tree bifurcations" Hippokratia 2014, 18, 1: 12-16.

Knight et al., "Choosing the optimal wall shear parameter for the prediction of plaque location—A patient-specific computational study in human right corornary arteries." Elsevier Inc., Aug. 2010, vol. 211, Issue 2, pp. 445-450.

Chinushi et al., "Blood Pressure and Autonomic Responses to Electrical Stimulation of the Renal Arterial Nerves Before and After Ablation of the Renal Artery." Hypertension, 2013, 61, pp. 450-456.

Pokushalov et al., "A Randomized Comparison of Pulmonary Vein Isolation With Versus Without Concomitant Renal Artery Denervation in Patients With Refractory Symptomatic Atrial Fibrillation and Resistant Hypertension." Journal of the American College of Cardiology, 2012, 8 pages.

Allen. E.V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New Engiand Journal of Med, Aug. 2009, 361; 9, 3 pages.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.

Page, I.H. et al., "The Effect of Renal Denervation on Patients Suffering From Nephritis," Feb. 27, 1935;443-458.

Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009, 4 pages.

Schlaich, M.P. et al., "Renal Denervation as a Therapeutic Approach for Hypertension: Novel Implications for an Old Concept," Hypertension, 2009; 54:1195-1201.

(56) References Cited

OTHER PUBLICATIONS

Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation far resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Search Report dated Oct. 17, 2013 for European Application No. 13159256.
International Searching Authority, International Search Report and Written Opinion dated Feb. 12, 2018 for PCT Application No. PCT/US2017/058731, 19 pages.

\* cited by examiner

METHODS AND SYSTEMS FOR OPTIMIZING PERIVASCULAR NEUROMODULATION THERAPY USING COMPUTATIONAL FLUID DYNAMICS

TECHNICAL FIELD

The present technology is related to perivascular neuromodulation. In particular, various embodiments of the present technology are related to methods and systems for informed decision-making regarding whether to deliver neuromodulation therapy to various regions of a target blood vessel.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Figure 1:
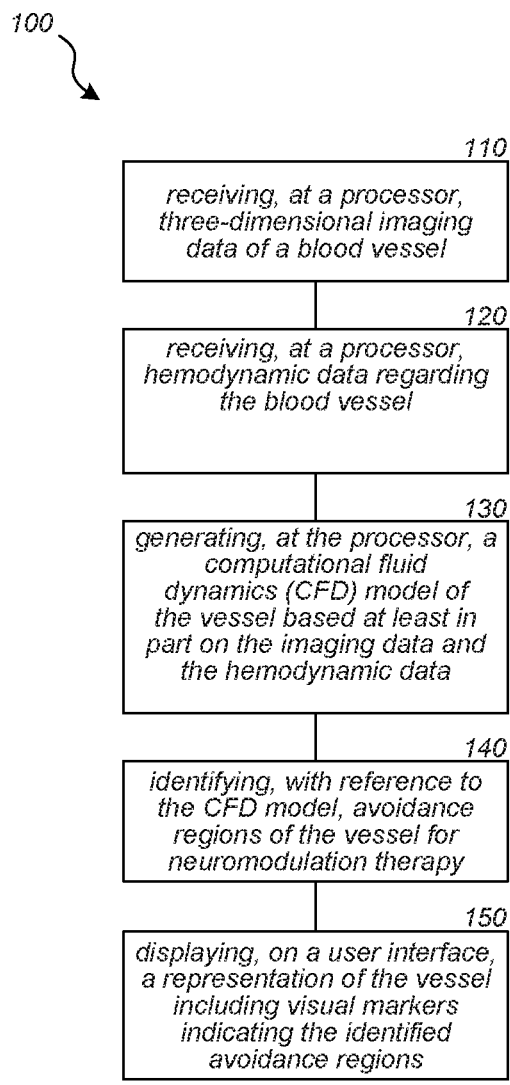
FIG. 1 is a block diagram illustrating a method of evaluating a blood vessel for neuromodulation therapy based on a computational fluid dynamics (CFD) model in accordance with an embodiment of the present technology.

Methods and systems in accordance with embodiments of the present technology can be configured to detect hemodynamic parameters of a patient's blood vessel, generate one or more models of the vessel, and analyze region(s) of the vessel to inform decision-making regarding potential regions for delivering neuromodulation therapy. Regions of the vessel may be identified for delivering therapy (e.g., target regions) while other regions may be identified as unsuitable for the therapy (e.g., avoidance regions). Specific details of several embodiments of the present technology are described herein with reference to FIGS. 1-18. Although many of the embodiments are described with respect to devices, systems, and methods for catheter-based perivascular renal neuromodulation, other applications and other embodiments in addition to those described herein are within the scope of the present technology. For example, at least some embodiments of the present technology may be useful for intraluminal neuromodulation, extravascular neuromodulation, non-renal neuromodulation, and/or use in therapies other than neuromodulation.

It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation catheter). The terms, "distal" and "distally" refer to a position distant from or in a direction away from a clinician or a clinician's control device along the length of device. The terms "proximal" and "proximally" refer to a position near or in a direction toward a clinician or a clinician's control device along the length of device. The headings provided herein are for convenience only and should not be construed as limiting the subject matter disclosed.

I. Selected Embodiments of Systems for Evaluating a Vessel for Neuromodulation Therapy and Associated Methods Renal perivascular neuromodulation therapy aims to modulate the autonomic nervous system, specifically the SNS, by modulating or destroying renal efferent sympathetic nerves and afferent renal sensory nerves. However, delivering neuromodulation therapy in a vessel at a location having a local flow abnormality and/or a region of secondary flow increases a risk that a patient could experience an unwanted event in response to therapy. Local flow abnormalities and/or regions of secondary flow are not visible with conventional methods of vascular imaging, such as fluoroscopy. Therefore, the patient can benefit from methods and systems configured to display or otherwise inform a user (e.g., a clinician) of locations in the target blood vessel having local flow abnormalities and/or regions of secondary flow. In this way, the clinician can reduce the risk of an unwanted event by avoiding delivering neuromodulation therapy at these locations. The present technology includes several embodiments of methods and systems for avoiding delivering neuromodulation therapy to locations in the vessel having local flow abnormalities and/or regions of secondary flow. These methods and systems are configured to provide visual, audible, and/or tactile feedback to guide positioning of a neuromodulation catheter 210 at one or more suitable therapeutic locations in the patient's vessel.

FIG. 1 is a block diagram illustrating a method 100 of evaluating a blood vessel for delivery of neuromodulation therapy based on a computational fluid dynamics (CFD) model in accordance with an embodiment of the present technology. As shown in FIG. 1, the method 100 includes receiving digital three-dimensional imaging data regarding a blood vessel at a processor (block 110). The three-dimensional imaging data of the vessel can represent a renal artery, a pulmonary artery, a hepatic artery, a coronary artery, an aorta, and/or other blood vessels suitable for neuromodulation therapy. In some embodiments, the vessel can be a main vessel (e.g., renal artery), at least one branch vessel of the main vessel (e.g., posterior or anterior branch of the renal artery), at least one accessory vessel directly coupled to the branch vessel (e.g., inferior anterior segmental artery or interior segmental artery) or another vessel coupled to the main vessel (e.g., aorta), and/or a combination thereof. The digital three-dimensional imaging data can be generated, in part, using input from one or more of the following modalities: angiography (e.g., x-ray, single-view, multi-view, computed tomography, positron emission, single positron emission), ultrasound, digital x-ray (e.g., contrast), digital fluoroscopy, magnetic resonance imaging (MRI) (e.g., contrast or non-contrast), computed tomography (CT) (e.g., spiral, helical, dual source), and/or a modality otherwise suitable for generating three-dimensional imaging input in a digital format. The three-dimensional imaging data can include information about one or more features of the blood vessel. For example, the information can include data corresponding to at least one dimension of a feature of the vessel, such as a cross-sectional area, a cross-sectional diameter, a volume, a length, and/or a combination thereof. In other embodiments, the feature can be a vessel wall or portion thereof (e.g., adventitia, media, and intima), a lumen, a branch, a bifurcation, a carina, an ostium, a taper region, an aneurysm, fibromuscular dysplasia, an occlusion, an impingement, a calcification, an intimal deposit, and/or a combination thereof. These features are described in detail below with reference to FIGS. 7-9.

In addition to receiving the three-dimensional imaging data at the processor, the method 100 includes receiving hemodynamic data regarding the blood vessel sensors (block 120). For example, the received hemodynamic data can be measurement of blood pressure, blood flow, blood impedance, viscosity of the patient's blood, other hemodynamic parameters, and/or combinations thereof. The received hemodynamic data can be based on measurements taken inside the vessel, outside the vessel, outside the patient's body, and/or a combination thereof. Blood viscosity can be assumed or measured. For example, blood viscosity is assumed to be $3\times10^{-3}$ to $4\times10^{-3}$ pascal-seconds (e.g., similar to water).

The blood pressure data, blood flow data, blood impedance data, and/or a combination thereof can be measured by one or more sensors, such as a sensor coupled to a neuromodulation catheter positioned in the target blood vessel in accordance with the present technology. In some embodiments, the method 100 includes coupling a sensor to the patient to detect and record data corresponding to one or more hemodynamic parameters either before or during an intravascular treatment. The sensor can be an external device that is coupled to the patient, for example, positioned near the patient's vessel. For example, the sensor can be an external pressure cuff, a Doppler ultrasound flow meter, a magnetic resonance imaging (MRI) machine, and/or combinations thereof. The sensor can alternatively be an internal device positioned within the patient, such as delivered transluminally into the patient's vessel. For example, the sensor can be coupled to a neuromodulation catheter 210 that can be delivered transluminally into the vessel. The transluminally delivered neuromodulation catheter can be positioned within a portion of the patient's vessel having laminar flow, and/or otherwise positioned to perform measurements of one or more hemodynamic parameters. The sensor can include, for example, a blood flow sensor, a blood pressure sensor, a blood impedance sensor, and/or a combination thereof. For example, the sensor can be a combination blood pressure-blood flow sensor carried by a guidewire (e.g., the blood pressure and blood flow sensor(s) can be the same sensor or different sensors located on the same guidewire) such as a fractional flow reserve (FFR) guidewire. In some embodiments, the combination guidewire also includes a transducer. In some embodiments, the method 100 can include coupling more than one sensor to the patient.

Several embodiments of the method 100 include measuring blood flow, blood pressure, and/or blood impedance in a main portion of the vessel (e.g., renal artery) and/or a branch of the main artery (e.g., anterior and/or posterior branch of renal artery). The measurements can be performed in a portion of the main vessel, or branch thereof, having stable (e.g., laminar) flow, a portion having unstable (e.g., turbulent, varied, secondary) flow, and/or a combination thereof.

After receiving the hemodynamic data, the method 100 continues by generating a computational fluid dynamics (CFD) model or representation of the target vessel based at least in part on the three-dimensional imaging data of the vessel (block 110) and the hemodynamic data (block 120). Using equations, algorithms, and various statistical methods, information regarding the three-dimensional imaging data of the vessel (e.g., vessel geometry) and hemodynamic data (e.g., blood pressure, blood flow, blood impedance, and/or blood viscosity) can be used to generate the CFD model of the vessel. The CFD model can be generated using a CFD workflow or other suitable methods for generating the CFD representation. The CFD workflow begins by fabricating a volumetric mesh to align with certain features of the vessel (e.g., geometry) represented by the three-dimensional imaging data. The hemodynamic data (e.g., blood flow data and/or blood pressure data) can be used to form one or more boundary conditions of the CFD simulation (e.g., the inlet) in the CFD workflow. The CFD workflow can generate a flow field and, if more than one CFD model is generated (e.g., different CFD models can be generated for certain portion of the vessel), the CFD models can be coupled (e.g., at the outlets) such that blood flow/blood pressure relationships can be computed. In some embodiments, the blood pressure data can be a proximal boundary condition and each outlet (e.g., distal boundary) can be coupled to a zero-dimensional representation of blood impedance, resistance, and compliance/capacitance of the patient's circulation distal to the boundaries. The CFD model can be displayed using one resolution in an image or multiple resolutions in a single representation. For example, a first portion of the CFD model can have a lower resolution compared to a second portion. Use of the lower resolution in the first portion is expected to reduce duration of certain computing parameters such that the CFD model having at least two resolutions can be generated faster than a CFD model having the resolution of the second portion displayed across the CFD model. In some embodiments, the CFD model can be validated using suitable validation methodologies (e.g., invasively measured values).

The user (e.g., clinician) and/or a computer can form certain assumptions about one or more features of the vessel physiology and hemodynamics or other information input into the CFD model. For example, an assumption can be that blood behaves as an incompressible fluid and/or a region of the vessel (e.g., segmented region) has rigid walls. In some embodiments, one or more hemodynamic parameters can be derived from empirical data, conglomerate data, and/or a combination thereof. In these embodiments, the CFD model of the vessel can be generated, in part, by applying one or more hemodynamic parameters derived from empirical data or conglomerate data to the CFD workflow. Empirical data can be obtained from a population database generated by the user or another party. The population database can include blood pressure data and/or blood flow data, each of which can be generalized. For example, generalized blood pressure can be 120/80 mmHg and generalized blood flow can be 500 ml/min. In additional embodiments, the CFD representation can include sample waveforms (e.g., measured, calculated, or standard) using computational methods such as ensemble averaging.

The CFD model is expected to aid in characterization and display of conventionally difficult to measure physiological and pathological parameters throughout the vessel targeted for perivascular denervation. CFD models are expected to quickly and accurately provide information regarding the vessel using anatomically accurate geometry and hemodynamically accurate inputs of the vessel. Iterative processing of CFD models can achieve convergence regarding physiological and pathological aspects of the modeled vessel(s). Measuring vessel wall shear stress ("WSS") is difficult and invasive without CFD models which can map spatial distribution of WSS, one of several physiological features that may be desirable to avoid when delivering neuromodulation therapy.

Based on the CFD model generated by the processor (block 130), the method 100 can continue by identifying, with the processor, target regions and/or avoidance regions of the vessel for delivering neuromodulation therapy (block 140). Locations of avoidance regions can be identified on the CFD model by the processor using equations, algorithms, various statistical methods, and/or analysis of the patient's anatomical features, by user observation, and/or by a combination thereof. The avoidance regions can be one or more regions of the vessel having a local flow abnormality, a physiologic feature, and/or a pathologic feature (e.g., diseases) (collectively "flow abnormality"). In some embodiments, flow abnormalities are associated with an increased risk of an unwanted event following neuromodulation therapy. Local flow abnormalities can include, but are not limited to, a region of secondary flow (e.g., turbulent flow, flow separation, and eddy formation), flow impingement, low WSS, high WSS, and/or WSS gradients. Avoidance regions can include one or more pathologic features of vascular disease (e.g., a calcification, a fibromuscular dysplasia, an aneurysm) and/or one or more physiologic features of the vessel (e.g., an ostium, a carina, a taper region, a bifurcation) and/or a combination thereof. In other embodiments (not shown), the method 100 can include identifying, via the processor, target regions of the vessel suitable for neuromodulation therapy The target regions, for example, can be one or more regions of the vessel lacking a local flow abnormality, a physiologic feature, and/or a pathologic feature associated with an increased risk of an unwanted event following neuromodulation therapy.

The target regions can be identified by determining if measured values of the hemodynamic parameters at a given location are within "normal" ranges or above/below values of the hemodynamic parameters indicative of no local flow abnormalities and/or no regions of secondary flow (e.g., threshold hemodynamic parameters). For example, if the hemodynamic parameter is blood pressure, then a blood pressure value within the "normal" range for blood pressure at the given location could trigger a recommendation to deliver neuromodulation therapy at the given location (e.g., a target region). Similarly, the avoidance regions can be identified by determining if measured values of the hemodynamic parameters at the given location are outside "normal" ranges or below/above the values of the hemodynamic parameters indicative of local flow abnormalities and/or regions of secondary flow. For example, a blood pressure value outside of the "normal" range for blood pressure at the given location could trigger a recommendation to avoid delivering neuromodulation therapy at the given location (e.g., an avoidance region). Each corresponding threshold hemodynamic parameter can be determined using empirical, conglomerate, or other suitable data useful to establish the threshold hemodynamic parameter. For example, threshold hemodynamic parameters can be determined for blood flow, blood pressure, blood impedance, and/or other hemodynamic parameters measured using the methods described herein.

The method 100 may use an algorithm executed by the processor to compare one or more hemodynamic parameters against one or more threshold hemodynamic parameters. The threshold hemodynamic parameter can be predetermined or can be calculated before performing the comparison. In some embodiments, the processor that analyzes the hemodynamic parameters can include algorithms that remove any apparent irregular hemodynamic parameter(s) to automatically correct for the anomalies. In other embodiments, the comparison between the one or more hemodynamic parameters and one or more threshold hemodynamic parameters can be made by users, systems, devices, and/or a combination thereof. In further embodiments, the algorithm can use two or more hemodynamic parameters and/or other data to provide a combined hemodynamic parameter that is more closely tied to identifying target and/or avoidance regions of the vessel than any one individual hemodynamic parameter alone.

The method 100 optionally continues by displaying a representation of the vessel including visual markers indicating one or more avoidance regions for not delivering neuromodulation therapy on a user interface (block 150). Also see FIG. 4 and corresponding description below. In some embodiments (not shown), the displayed representation can also include markers of one or more target regions of the vessel for delivering neuromodulation therapy. In other embodiments, the representation can have more than one portion of the vessel displayed, such as a first portion and a second portion. The first portion and the second portion can be contiguous or separated (e.g., a different portion separates the first portion from the second portion). The displayed first portion can correspond to one or more regions suitable for delivering neuromodulation therapy (e.g., target regions), whereas the displayed second portion can correspond to one or more avoidance regions to avoid delivering neuromodulation therapy. Different features of the representation can be displayed using different resolutions. Each of the avoidance regions and the target regions can be visually displayed on the representation using unique corresponding indicia such as colors, shading, patterns, shapes, and/or combinations thereof. For example, the avoidance regions could be displayed on the representation using a red, round shape (e.g., a red circle) encompassing the avoidance regions whereas target regions could be displayed using a green, round shape (e.g., a green circle) around the target regions. Similarly, avoidance regions could be displayed using a shape having a red color gradient with a center of the avoidance regions colored a dark red and the sides colored in a pale red. Target regions could be similarly displayed with green gradient colored shapes. In some embodiments, potential vessel treatment having no data or inconclusive data could be encompassed with a yellow round shape (e.g., yellow circle) having a solid color or a gradient of color. In other embodiments, different colors, patterns, and shapes (e.g., arrows) could be displayed to indicate avoidance regions, target regions, and potential regions. The CFD model information thus provided to the clinician can be used to optimize the neuromodulation procedure.

With reference to the vessel evaluation results displayed on the user interface, the clinician can deliver neuromodulation catheter 210 to the patient's vessel while monitoring the location of the catheter within the vessel. As described in greater detail below with reference to FIG. 10, the neuromodulation catheter can be delivered to the patient's vessel using the methods described herein in accordance with the present technology or, alternatively, using other methods suitable for delivering the catheter. For example, the location of a portion of the neuromodulation catheter (e.g., neuromodulation assembly 230) can be monitored while the catheter is being positioned within the vessel. In some embodiments, the location can be monitored by visually observing assembly 230 during delivery to the vessel. Alternatively, data regarding the current location (e.g., monitored location) of assembly 230 in the vessel can be sent to the processor, e.g. by a signal emitted by a transmitter incorporated in or otherwise coupled to the neuromodulation catheter. The user can receive the feedback signal via user interface and/or another signal emitting device configured to emit the visual, audio, and/or tactile signal in accordance with embodiments of the present technology. In certain embodiments, the location of the neuromodulation assembly can be monitored in real-time.

In further embodiments, after receiving the catheter location data, the processor can provide a recommendation to the user of whether to proceed with neuromodulation therapy based on whether the current location of assembly 230 includes an identified avoidance region and/or target region. The recommendation can include recommending the user avoid delivering neuromodulation therapy to the one or more identified regions of the patient's vessel (e.g., an avoidance region) or recommending the user deliver neuromodulation therapy to the one or more identified regions (e.g., a target region). In some embodiments, the recommendation can be provided while delivering and/or positioning the neuromodulation catheter. In other embodiments, the recommendation can be provided before or after delivering and/or positioning the catheter.

In some embodiments, the recommendation can be provided to the user via the user interface, for example, by displaying the recommendation on a display or emitting a signal. The signal can be a visual signal, an audio signal, a tactile signal, or a combination thereof. For example, the visual signal can be emitted by a device (e.g., a light) that turns on when assembly 230 is positioned proximate to the one or more identified regions. For example, the recommendation can be a light that turns green when assembly 230 is positioned proximate to or within an identified target region and/or a light that turns red when positioned proximate to or within an identified avoidance region. In other embodiments, the device can be a speaker, a vibration mechanism, or other device suitable for conveying the signal to the user. In addition to the display and/or signal, the recommendation can be provided to the user by exhibiting one or more of the hemodynamic parameters and/or an overall hemodynamic parameter on a visual display or other device configured to receive the hemodynamic parameter(s) and provide the recommendation. In further embodiments, the three-dimensional representation, CFD model, and/or other representation can be stored to guide positioning of the neuromodulation catheter at a later time, and/or computations performed after the image and/or representations were obtained and/or generated. In these embodiments, the image and/or representations can be stored, analyzed, and/or computations performed using a component of the device and/or environment. Furthermore, the processor can also provide a report that distributes the hemodynamic parameters to the user on a smart phone, a computer, a tablet computer, and/or other device including a digital display.

A method of the present technology can include applying neuromodulation energy to at least one of the target regions using a neuromodulation catheter 210. In other embodiments, the target region(s) can be marked as locations for future neuromodulation therapy. When one or more of the hemodynamic parameter(s) are elevated above a corresponding threshold hemodynamic parameter(s) at a location, the location can be identified as an avoidance region. If neuromodulation energy were to be delivered at an identified avoidance region, there is a concern that the patient could have sequelae, such as swelling, edema, stenosis, a tear, rupture, dilation, dissection, and/or thrombus, associated with delivering neuromodulation therapy at that location.

In further embodiments, the method and systems described herein can be used to monitor the vessel following neuromodulation therapy to determine if an unwanted event has occurred or might occur. Changes in blood flow and/or blood pressure following neuromodulation therapy can indicate that an unwanted event might occur at one or more of the regions, or at another region of the vessel. If an unwanted event does occur, the user can opt to treat the patient accordingly.

II. Selected Embodiments of Neuromodulation Systems

Figure 2:
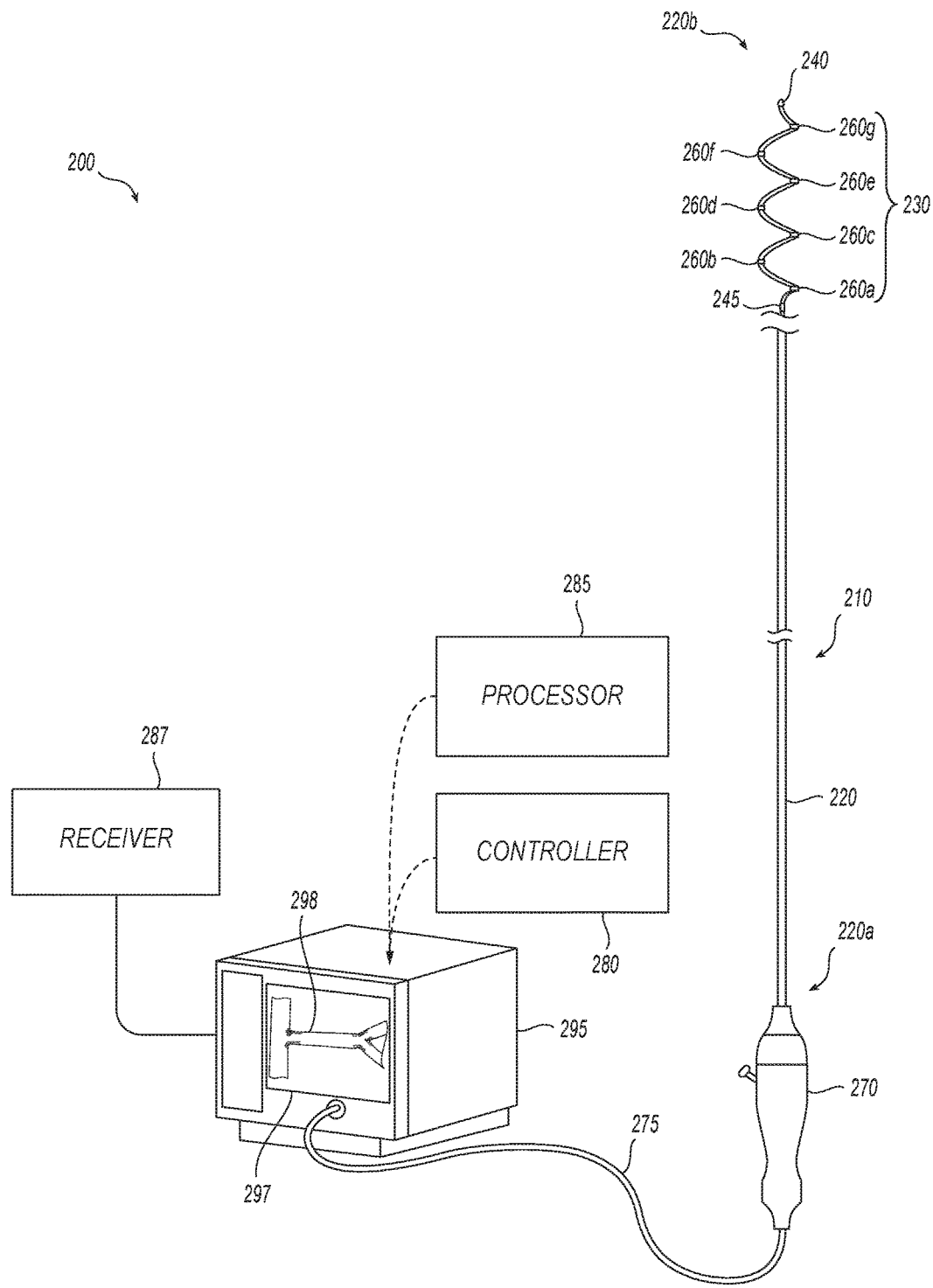
FIG. 2 is a partially schematic illustration of a neuromodulation system configured in accordance with an embodiment of the present technology.

FIG. 2 is a partially schematic illustration of a neuromodulation system 200 ("system 200") in accordance with an embodiment of the present technology. The system 200 can be used in conjunction with method 100 described above with references to FIG. 1 to assess one or more hemodynamic parameters and/or identify one or more avoidance regions and/or target regions for delivering neuromodulation therapy. In addition, the system 200 and embodiments thereof can be used to deliver neuromodulation therapy to the patient.

As shown in FIG. 2, the system 200 includes a neuromodulation catheter 210, a console 295, and a cable 275 operatively coupling the neuromodulation catheter 210 to the console 295. The neuromodulation catheter 210 includes an elongated shaft 220 having a proximal portion 220a and a distal portion 220b, a handle 270 operably connected to the shaft 220 at the proximal portion 220a, and a neuromodulation assembly 230 at the distal portion 220b of the shaft 220. The distal portion 220b of the shaft 220 is configured to be moved within a lumen of the patient and locate the neuromodulation assembly 230 at a target region within the lumen. For example, the shaft 220 can be configured to position the neuromodulation assembly 230 within a blood vessel, a duct, an airway, or another naturally occurring lumen within the human body.

The shaft 220 and the neuromodulation assembly 230 can be 2, 3, 4, 5, 7, or 8 French size or another suitable size. The dimensions (e.g., outer diameter and length) of the distal portion 220b of the shaft 220 can be selected to accommodate the vessels or other body lumens in which the distal portion 220b of the neuromodulation catheter 210 is designed to be delivered. For example, the axial length of the distal portion 220b, may be selected to be no longer than a patient's renal artery (e.g., typically less than 8 cm), and have a deployed or expanded diameter that accommodates the inner diameter of a typical renal artery and/or the branches of the renal artery (e.g., about 2-10 mm, e.g., about 4-8 mm, for the renal artery RA, etc.). In addition, the neuromodulation assembly 230 can include a shape memory portion having shape memory material, such as nickel-titanium alloy, that imparts a helical or spiral shape to the neuromodulation assembly 230 when expanded. In other embodiments, the shaped portion of the neuromodulation assembly 230 can have other dimensions depending on the body lumen within which it is configured to be deployed.

As illustrated, the neuromodulation assembly 230 includes a sensor 240, a transmitter 245, and a plurality of energy delivery elements 260a-g (collectively energy delivery elements 260). In this embodiment, the sensor 240 is disposed at the distal end (e.g., terminal tip) of the distal portion 220b and the transmitter 245 is disposed proximal to the energy delivery elements 260. In other embodiments, the sensor 240 and/or the transmitter 245 can be disposed at different locations suitable for the sensor 240 to detect one or more hemodynamic parameters and/or for the transmitter 245 to transmit the location of the neuromodulation assembly 230 to a receiver 287 in accordance with embodiments described herein. For example, the sensor 240 can be proximal to and/or the transmitter 245 can be distal to one or more energy delivery elements 260. The sensor 240 and the transmitter 245 can be connected to one or more supply wires (not shown) that convey energy to the sensor 240 and transmitter 245. Alternatively, the sensor 240 and/or the transmitter 245 can be coupled operatively to the console 295 by dedicated wires and/or wirelessly (e.g., Bluetooth, radio wave, etc.). In embodiments where neither the sensor 240 nor the transmitter 245 is located at the catheter distal end, the neuromodulation assembly 230 can have an atraumatic tip (not shown). In certain embodiments, the neuromodulation assembly 230 can include more than one sensor 240 and/or transmitter 245. The sensor 240, the transmitter 245 and the neuromodulation assembly 230 can be integrated into a single neuromodulation catheter 210 as illustrated, or one or more of the sensors 240 and/or the transmitters 245 can be provided separately from the neuromodulation catheter 210, as will be discussed below.

The sensor 240 can detect a physiological parameter, such as a hemodynamic parameter, and the transmitter 245 can communicate to the receiver 287 a signal related to the location of the neuromodulation assembly 230 in the vessel. The sensor 240 can include one or more sensors, for example, a blood velocity sensor (e.g., a Doppler laser velocity sensor or an ultrasonic flow meter) that can detect blood flow through a vessel (e.g., renal artery RA), a pressure sensor that measures the blood pressure within the vessel, a blood impedance sensor (e.g., single or multi-electrode) that can determine changes in vessel diameter, and/or other suitable sensors for detecting one or more hemodynamic parameters. As will be appreciated by those skilled in the art, blood is more conductive than vessel tissue and, therefore, vessel impedance, i.e. blood impedance is lower when the vessel has a larger diameter (i.e., when more blood is contained in the vessel) and higher when the vessel has a smaller diameter (i.e., when less blood is contained in the vessel). Accordingly, when the sensor 240 is a single or multi-electrode impedance sensor, blood impedance measurements taken by the sensor 240 can be correlated to changes in vessel diameter, segmental volume, and/or cross-sectional area (i.e., a hemodynamic response). In some embodiments, the blood impedance measurements can be used to assess the efficacy of the neuromodulation treatment. Similar to vessel diameter, blood flow and blood pressure are expected to change in response to a stimulus, and these changes are expected to occur to a lesser degree after neuromodulation than before neuromodulation. Therefore, the changes in blood flow and/or vessel pressure measurements caused by an electrical or pharmacological stimulus can be detected before and after neuromodulation and then compared to threshold values to determine the efficacy of neuromodulation therapy. Further embodiments of monitoring hemodynamic responses to stimuli are disclosed in PCT Patent Application Number PCT/US15/534999, filed Oct. 1, 2015, entitled "Systems and Methods for Evaluating Neuromodulation Therapy via Hemodynamic Responses", which is incorporated by reference herein in its entirety.

In some embodiments, the sensor 240 can detect more than one hemodynamic parameter in the vessel. For example, the sensor 240 can include a sensor configured to detect blood flow and blood pressure in the renal artery. In other embodiments, the sensor 240 can include different or additional sensors that detect and/or record other information such as one or more of temperature (e.g., thermocouple, thermistor, etc.), optical, chemical, and/or other parameters. The sensor 240 sensor(s) can further be configured to record data associated with the detected hemodynamic parameters. In some embodiments, the recordings can be made by another component of the system 200.

The transmitter 245 can include one or more sensors, for example, a first sensor, a second sensor, a third sensor, a fourth sensor, etc. configured to monitor the location of the neuromodulation assembly 230 in the vessel. In some embodiments, each sensor of the transmitter 245 can be configured to monitor the location of specific energy delivery elements 260 (e.g., electrodes). For example, the first sensor can be configured to monitor a location of energy delivery elements 260a and 260b, the second sensor can be configured to monitor the location of energy delivery elements 260c and 260d, the third sensor can be configured to monitor the location of energy delivery elements 260e and 260f, and the fourth sensor can be configured to monitor the location of energy delivery element 260g. In other embodiments, each sensor can have a certain range and can monitor the location of any portion of the neuromodulation assembly 230, or the location of the transmitter relative to any features of the vessel (e.g., wall, ostium, bifurcation, etc.) located within the range. The sensor(s) of the transmitter 245 can further be configured to record data associated with the monitored location. In some embodiments, the location recordings can be made by another component of the system 200.

In other embodiments, the neuromodulation assembly 230 can have fewer or more than seven energy delivery elements 260. As illustrated in FIG. 2, the neuromodulation assembly 230 includes seven energy delivery elements 260a-g. The energy delivery elements 260 can be configured to apply electrical stimuli (e.g., RF energy) to identified target regions at or proximate to one or more vessels within the patient, to temporarily stun nerves, and/or to deliver neuromodulation energy to target regions. The energy delivery elements 260 can be connected to one or more supply wires (not shown) that convey energy to the energy delivery elements 260. In some embodiments, the energy delivery elements 260 are electrodes. In various embodiments, certain energy delivery elements 260 can be dedicated to applying stimuli, and other energy delivery elements 260 can be other types of therapeutic elements, such as transducers or other elements, to deliver energy to modulate perivascular nerves using other suitable neuromodulation modalities, such as pulsed electrical energy, microwave energy, optical energy, ultrasound energy (e.g., intravascularly delivered ultrasound, extracorporeal ultrasound, and/or high-intensity focused ultrasound (HIFU)), direct heat energy, radiation (e.g., infrared, visible, and/or gamma radiation), and/or other suitable types of energy. In certain embodiments, the neuromodulation catheter 210 may be configured for cryotherapeutic treatment, and can apply cryogenic cooling to the renal artery RA with a refrigerant (e.g., via a balloon catheter that circulates the refrigerant). In this embodiment, the system 200 can include a refrigerant reservoir (not shown) coupled to the neuromodulation catheter 210, and can be configured to supply the neuromodulation catheter 210 with refrigerant. In still other embodiments, the neuromodulation catheter 210 is configured for chemical-based treatment (e.g., drug infusion), and the neuromodulation catheter 210 can dispense intraluminally or inject transluminally one or more chemicals to the treatment region to effectuate neuromodulation. Such chemicals can include neurotoxins (e.g., ethanol), adrenergic antagonists (e.g., guanethidine), and/or tissue necrosis-inducing agents (e.g., ethyl alcohol). In this embodiment, the system 200 can include a chemical reservoir (not shown) and can be configured to supply the neuromodulation catheter 210 with one or more chemicals. In certain embodiments, one or more sensors and/or sensors may be located proximate to, within, or integral with the energy delivery elements 260.

The energy delivery elements 260 (e.g., electrodes) can be positioned on the neuromodulation assembly 230 in one or multiple planes in a variety of patterns. In the illustrated embodiment, the energy delivery elements 260 are positioned on the shape memory portion of the neuromodulation assembly 230 such that many or all of the energy delivery elements 260 press against or otherwise contact the interior vessel wall (e.g., renal artery RA wall). In other embodiments, multiple energy delivery elements 260 can be positioned in the same plane orthogonal to the renal artery RA to deliver stimuli and/or obtain multiple recordings in the same plane of the interior vessel wall. When in contact with the interior vessel wall, the energy delivery elements 260 and/or another type of energy delivery element can deliver neuromodulation energy to the target region to modulate or ablate nerves proximate to the target region. It is expected that a successful or effective neuromodulation treatment or therapy (i.e., when nerves are ablated to a desired degree) stops or attenuates nerve activity.

Although the illustrated embodiment of the neuromodulation assembly 230 is configured with the spiral/helix-shape, in other embodiments, the distal portion 220b of the shaft 220 can have other suitable shapes (e.g., semi-circular, curved, straight, etc.), and/or the neuromodulation catheter 210 can include multiple support members configured to carry one or more energy delivery elements 260 and press the energy delivery elements 260 against the interior vessel wall. Other suitable devices and technologies are described in, for example, U.S. patent application Ser. No. 12/910,631, filed Oct. 22, 2010; U.S. patent application Ser. No. 13/279,205, filed Oct. 21, 2011; U.S. patent application Ser. No. 13/279,330, filed Oct. 23, 2011; U.S. patent application Ser. No. 13/281,360, filed Oct. 25, 2011; U.S. patent application Ser. No. 13/281,361, filed Oct. 25, 2011; PCT Application No. PCT/US11/57754, filed Oct. 25, 2011; U.S. Provisional Patent Application No. 71/646,218, filed May 5, 2012; U.S. patent application Ser. No. 13/793,647, filed Mar. 11, 2013; U.S. Provisional Patent Application No. 71/961,874, filed Oct. 24, 2013; and U.S. patent application Ser. No. 13/670,452, filed Nov. 7, 2012. All of the foregoing applications are incorporated herein by reference in their entireties. Nonlimiting examples of devices and systems include the Symplicity™ RF ablation catheter and the Symplicity Spyral™ multielectrode RF ablation catheter.

The console 295 of system 200 can be configured to control, monitor, supply, and/or otherwise support operation of the neuromodulation catheter 210 and the CFD modeling of FIG. 1. As illustrated in FIG. 2, the console 295 includes a controller 280, a processor 285, the receiver 287, and a user interface 297. For example, the CFD models generated by method 100 and embodiments thereof can be displayed as one or more images 298 on the user interface 297. In other embodiments, rather than having the user interface 297 integrated with the console 295, the user interface can be a separate component, such as a monitor (not shown), that displays the image 298. In certain embodiments, the console 295 can have more than one user interface 297, or the system 200 can have both a separate monitor (not shown) and the user interface 297 integrated with the console 295. The console 295 can be configured to generate a selected form and/or magnitude of energy for delivery to tissue at the target region via the neuromodulation assembly 230, and therefore, the console 295 may have different configurations depending on the treatment modality of the neuromodulation catheter 210. For example, when the neuromodulation catheter 210 is configured for electrode-based, heat-element-based, or transducer-based treatment, the console 295 can include an energy generator (not shown) configured to generate RF energy (e.g., monopolar and/or bipolar RF energy), pulsed electrical energy, microwave energy, optical energy, ultrasound energy (e.g., intravascularly delivered ultrasound, extracorporeal ultrasound, and/or HIFU), direct heat energy, radiation (e.g., infrared, visible, and/or gamma radiation), and/or another suitable type of energy.

In selected embodiments, the console 295 and neuromodulation catheter 210 may be configured to deliver a monopolar electric field via one or more of the energy delivery elements 260. In such embodiments, a neutral or dispersive energy delivery element (not shown) may be electrically connected to the console 295 and attached to the exterior of the patient. In embodiments including multiple energy delivery elements 260, the energy delivery elements 260 may deliver power independently in a monopolar fashion, either simultaneously, selectively, or sequentially, and/or may deliver power between any desired combinations of the energy delivery elements 260 in a bipolar fashion. In addition, a user may manually select which energy delivery elements 260 are activated for power delivery in order to form highly customized lesion(s) within the lumen (e.g., renal artery), as desired.

The controller 280 and processor 285 can define a computing device that includes memory and is configured to receive and store imaging data, hemodynamic data (e.g., measured values of a hemodynamic parameter detected by the sensor 240) and/or the location data (e.g., magnetic signals transmitted by the transmitter 245). The memory can be configured to store instructions that, when executed by the computing device, cause the system 200 to perform certain operations in accordance with the present technology, such as executing embodiments of blocks 110, 120, 130, 140 and 150 of method 100 described above with respect to FIG. 1.

In addition to avoiding delivering neuromodulation energy at one or more avoidance regions as described above, additional embodiments of methods and systems of the present technology can determine efficacy and/or risk to optimize a neuromodulation procedure. For example, the sensor 240 can be positioned proximal to the treatment region to detect or measure one or more hemodynamic parameter(s) after applying neuromodulatory energy. In addition, the transmitter 245 can be positioned near (e.g., proximal or distal) to the treatment region to convey information to the user about the location of the neuromodulation assembly 230 in the vessel. The controller 280 can include algorithms that generate a comparison of the patient's pre-neuromodulation and post-neuromodulation information (e.g., hemodynamic parameters, imaging data, etc.). Since one or more hemodynamic parameters can change in response to energy delivery, the comparison can provide the user with an indication of whether neuromodulation therapy was effective, and/or whether there is risk of, or an actual unwanted event. In certain embodiments, the comparison can be referenced against a standardized or patient-specific threshold change or level indicative of therapeutically effective neuromodulation and/or a risk of an unwanted event. The comparison can be provided to the user via the user interface 297 or other component (e.g., a monitor). Based on the comparison, the user can determine whether the neuromodulation therapy achieved the desired effect, or if the therapy affected hemodynamic parameter(s) and/or a structural feature of the vessel (e.g., wall thickness, rupture, intimal delamination, etc.). If the comparison indicates that neuromodulation therapy was not effective and/or that the risk of experiencing an unwanted event has increased, subsequent monitoring and/or subsequent courses of treatment can be performed. For example, the neuromodulation assembly 230 can be repositioned along the vessel (e.g., renal artery RA) and/or rotated to modulate nerves at a different position or in a different plane.

Figure 3:
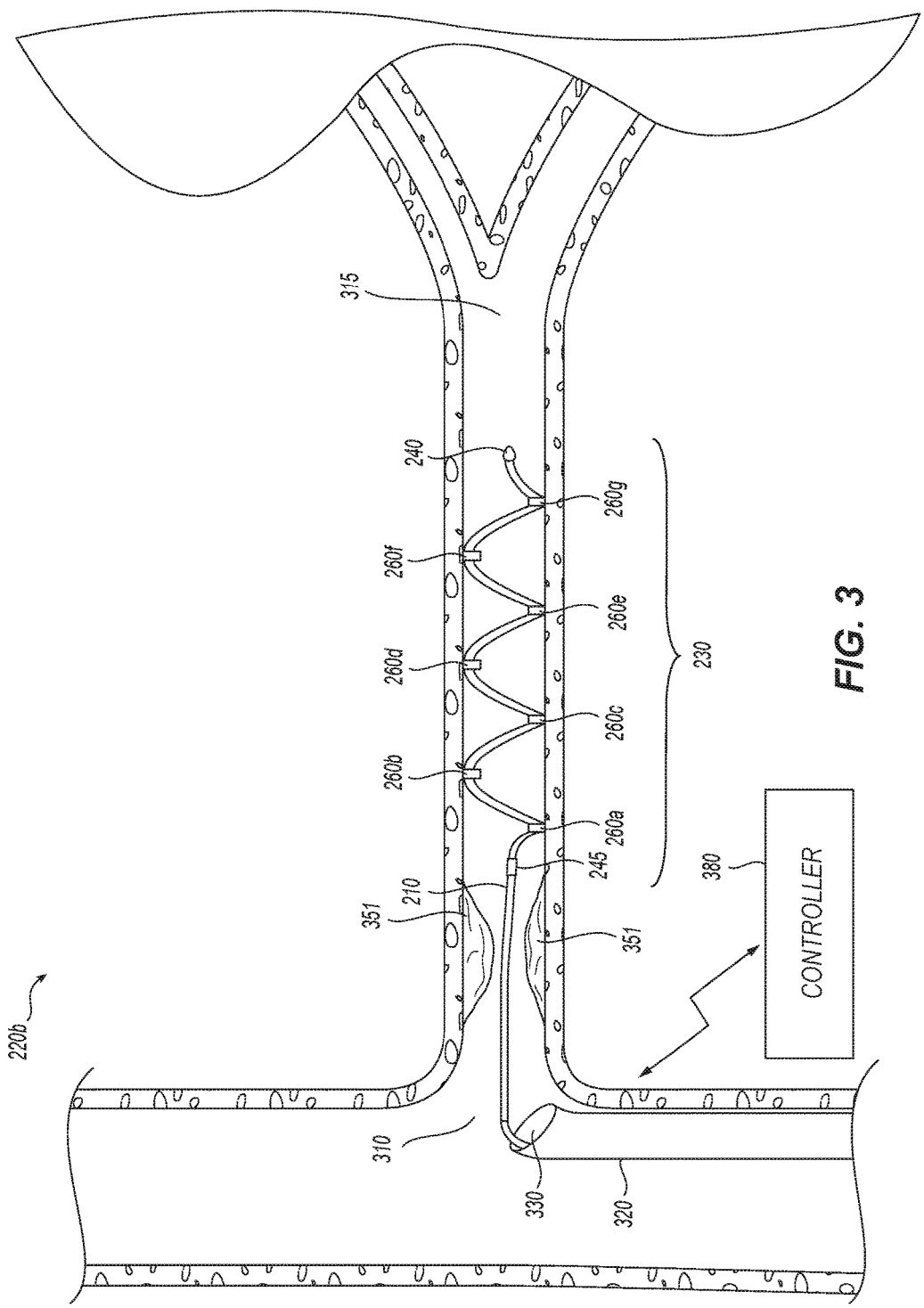
FIG. 3 is a side view of a distal portion of the neuromodulation catheter of FIG. 2 positioned within a blood vessel.

FIG. 3 is a side view of the neuromodulation assembly 230 of FIG. 2 positioned within a renal blood vessel in accordance with another embodiment of the present technology. In other embodiments, the neuromodulation catheter 210 may be positioned in other vessels for delivering neuromodulation therapy at different regions within the human patient. As illustrated, the system 200 includes a guide catheter 320 configured to locate the distal portion 220b of the neuromodulation catheter 210 intravascularly at a treatment region within the blood vessel (e.g., the renal artery RA). In operation, intraluminal delivery of the neuromodulation assembly 230 can include percutaneously inserting a guidewire (not shown) into a body lumen of a patient and moving the shaft 220 (FIG. 2) and/or the neuromodulation assembly 230 along the guidewire until the neuromodulation assembly 230 reaches a target region (e.g., a renal artery). For example, a distal end of the neuromodulation assembly 230 may define a passageway for engaging the guidewire for delivery of the neuromodulation assembly 230 using over-the-wire (OTW) or rapid exchange (RX) techniques. In other embodiments, the neuromodulation catheter 210 can be a steerable or non-steerable device configured for use without a guidewire. In still other embodiments, the neuromodulation catheter 210 can be configured for delivery via a sheath (not shown).

During a procedure, the neuromodulation assembly 230 extends distally of the distal portion 330 of the guide catheter 320 and into the vessel lumen. As the neuromodulation assembly 230 is advanced through the vessel lumen, for example, the sensor 240 senses laminar blood flow through a proximal portion of the lumen. When the neuromodulation assembly encounters potential avoidance regions such as a stenosis 351, and/or a bifurcation 315, the sensor 240 detects a change in the previously laminar blood flow. The sensor 240 transmits the blood flow data to the receiver 287 and, as described above, other components of the system 200 generate the CFD model based, in part, on the blood flow data. As described above, the system 200 identifies and recommends avoidance regions and target regions for delivering neuromodulation energy.

Once positioned in the target blood vessel, the neuromodulation assembly 230 is transformed from a low-profile delivery state (not shown) for delivery (e.g., intravascularly through the aorta) to a deployed state (e.g., radially expanded state). When deployed, the energy delivery elements 260 are pressed against the inner wall of the vessel and neuromodulation energy can be selectively delivered to the identified target regions. After delivering neuromodulation energy, the system 200 is configured to sense post-neuromodulation therapy parameters and determine the efficacy and/or the risk of an unwanted event as described above. If necessary, the user can reposition the neuromodulation assembly 230 to deliver additional neuromodulation therapy at one or more different identified target locations. To reposition the neuromodulation assembly 230, the user can return the assembly 230 to the low-profile delivery state and re-deploy the neuromodulation assembly 230 at a new location. In some embodiments, the location of the neuromodulation assembly 230 during positioning, deployment, repositioning, re-deployment, and/or a combination thereof can be displayed on the user interface 297 in real-time.

Figure 4:
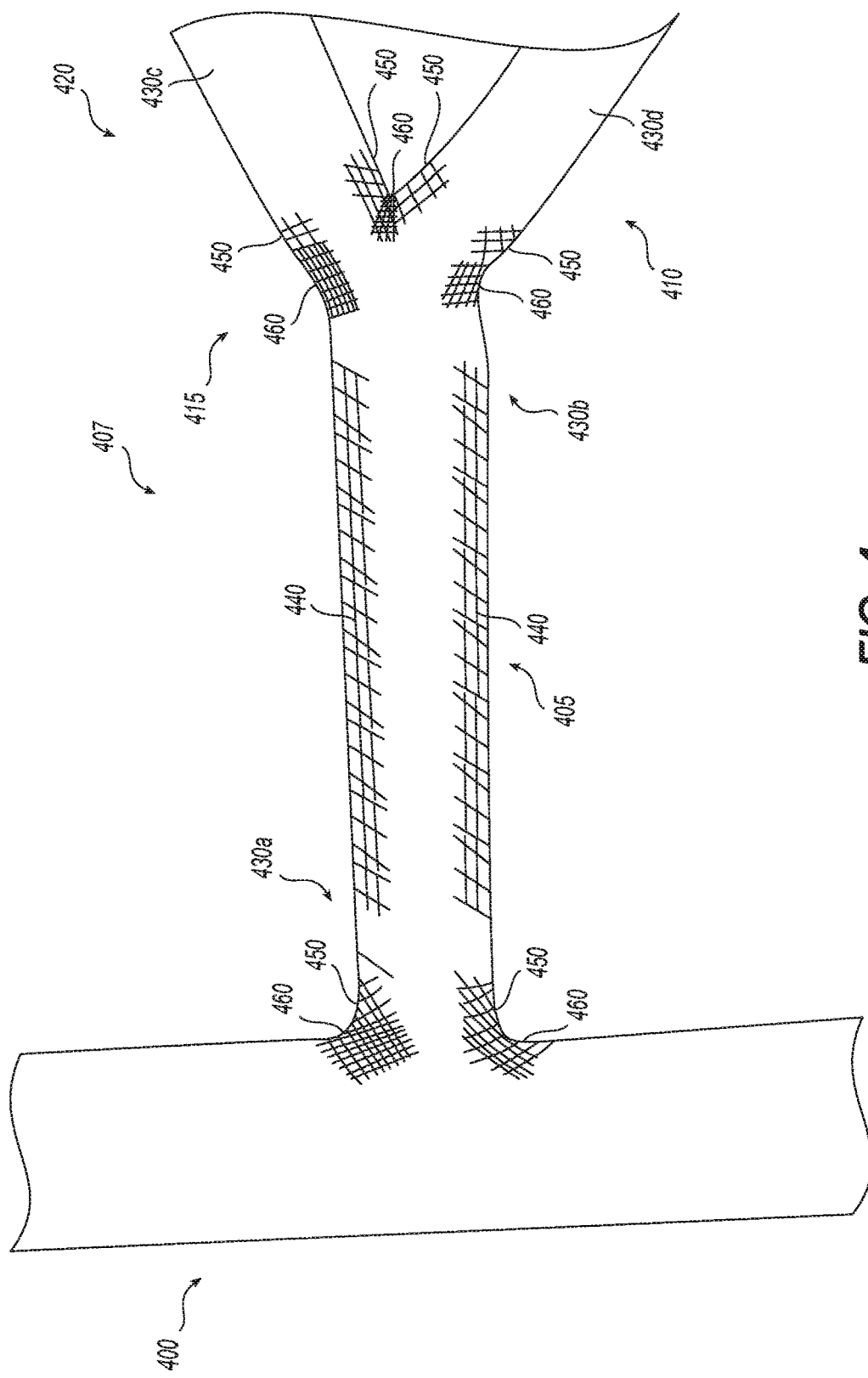
FIG. 4 is a graphical representation of a computational fluid dynamics model of a blood vessel in accordance with an embodiment of the present technology.

FIG. 4 illustrates a representation ("representation 400") of a blood vessel in accordance with an embodiment of the present technology. The representation 400 is a CFD image 407 displaying visual indicators corresponding to target regions 440, potential regions 450, and avoidance regions 460 determined in accordance with embodiments of blocks 110, 120, 130 and 140 of the method 100. The CFD image 407 depicts a vessel 405 including a proximal portion 430a and a distal portion 430b with a main portion of the vessel 405 extending there between. The CFD image 407 further depicts a right branch 410 and a left branch 420 extending from the vessel 405 at a bifurcation 415 into the right portion 430d and the left portion 430c, respectively. In the illustrated embodiment, avoidance regions 460 are indicated by dense hash marks, target regions 440 are indicated by sparse hash marks, and potential regions 450 are illustrated by moderate hash marks. In other embodiments, the avoidance regions 460, potential regions 450, and target regions 440 can be individually indicated by a color, a shade of the color, more than one color, more than one shade of the color, one or more patterns, shapes, and/or combinations thereof. For example, avoidance regions 460 could be indicated by a red marker, potential regions 450 by a yellow marker, and target regions 440 by a green marker, with each marker enclosing the boundaries of the corresponding region.

In some embodiments, the neuromodulation assembly 230 (not shown) can be positioned in the vessel 405 while the user is viewing the representation 400. Referring in part to FIGS. 2 and 3, for example, representation 400 can guide positioning of the neuromodulation assembly 230 in the vessel when the user can visually determine where the neuromodulation assembly 230 is positioned with respect to an avoidance region 460, a potential region 450, or a target region 440. Accordingly, the clinician can refer to the representation 400 and select or de-select particular energy delivery elements 260 to avoid delivering neuromodulation therapy to the patient at identified and displayed avoidance regions 460 and rather deliver therapy to the identified and displayed target regions 440.

In some embodiments, an audible signal, a tactile signal, or a combination thereof can be combined with the representation 400 to alert the user of a location of the neuromodulation assembly 230. For example, the audible signal and/or the tactile signal can alert the user when one or more energy delivery elements 260 of the neuromodulation assembly 230 are located at an identified avoidance region 460 or alternatively at an identified target region 440. Alternatively, the audible signal and/or the tactile signal can include multiple signals wherein each signal (e.g., a tone, a vibration, repetition of the signal, etc.) corresponds to a particular energy delivery element 260 positioned at a particular region. Using a multi-electrode catheter such as catheter 210, the clinician may operate console 295 to test each energy delivery element 260 individually for a signal indicating the potential risk or benefit of administering neuromodulation energy at each element's current location. For example, a first signal can correspond to an energy delivery element 260 located within an avoidance region 460, a second signal can correspond to a second energy delivery element 260 located within a potential region 450, and a third signal can correspond to a third energy delivery element 260 located within a target region 440. Similar to the displayed indicators, the audible signals and/or the tactile signals can be transmitted to the user in real-time as the neuromodulation assembly 230 is being positioned regardless of whether the location of the neuromodulation assembly 230 is visible on representation 400 in real-time. In certain embodiments, only visual indicators are displayed on the representation 400, only audible signals are transmitted to the user, or only tactile signals are transmitted to the user.

Figure 5:
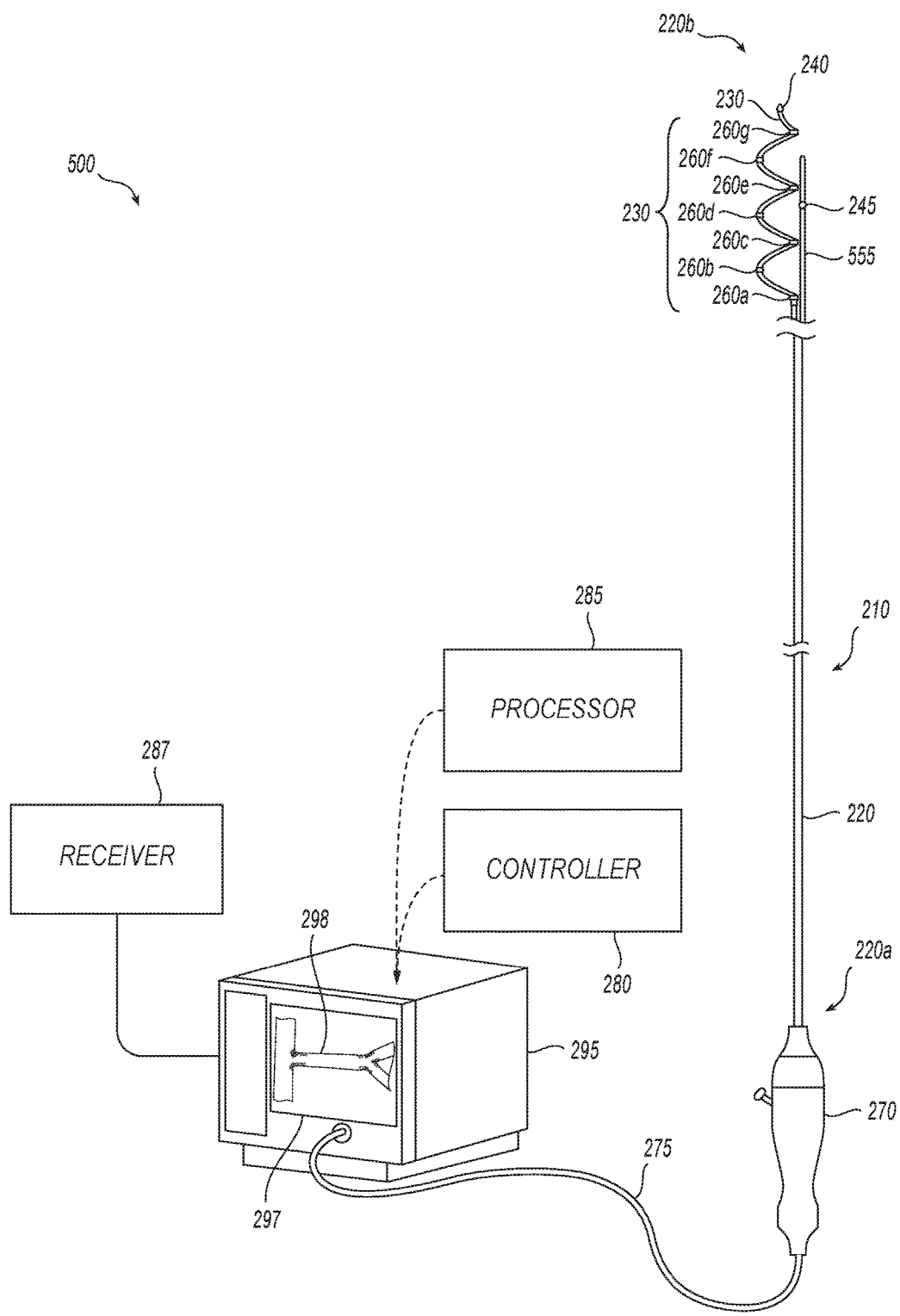
FIG. 5 is a partially schematic illustration of a neuromodulation system configured in accordance with another embodiment of the present technology.

FIG. 5 is a partially schematic illustration of a neuromodulation system 500 ("system 500") configured in accordance with another embodiment of the present technology. Certain features of system 500 are generally similar to other embodiments of the present technology described herein. The system 500 is different than the system 200 in that the transmitter 245 is carried by a separate catheter or guidewire 555. In the illustrated embodiment, the sensor 240 is at the distal-most end (e.g., tip) of the distal portion 220b and the transmitter is disposed along a length of the wire 555. In other embodiments, the sensor 240 can be elsewhere along a length of the distal portion 220b (e.g., on the neuromodulation assembly 230) and/or the transmitter 245 can be at the distal-most end (e.g., tip) of the guidewire 555. The shaft 220 and the guidewire 555 can be integrated into a single neuromodulation catheter 210 or, alternatively, they can be in separate components.

In other embodiments, the transmitter 245 can be at the distal portion 220b of the shaft 220 instead of the sensor, and the sensor 240 can be carried by the guidewire 555. In embodiments where the neuromodulation catheter 210 includes more than one sensor 240 and/or more than one transmitter 245, some of the sensors and/or some of the transmitters can be carried by the distal portion 220b of the shaft 220 and others can be carried by the guidewire 555. In other embodiments, the sensor 240 can be mounted on a portion of a guide catheter that is insertable into the vessel receiving neuromodulation treatment.

Figure 6:
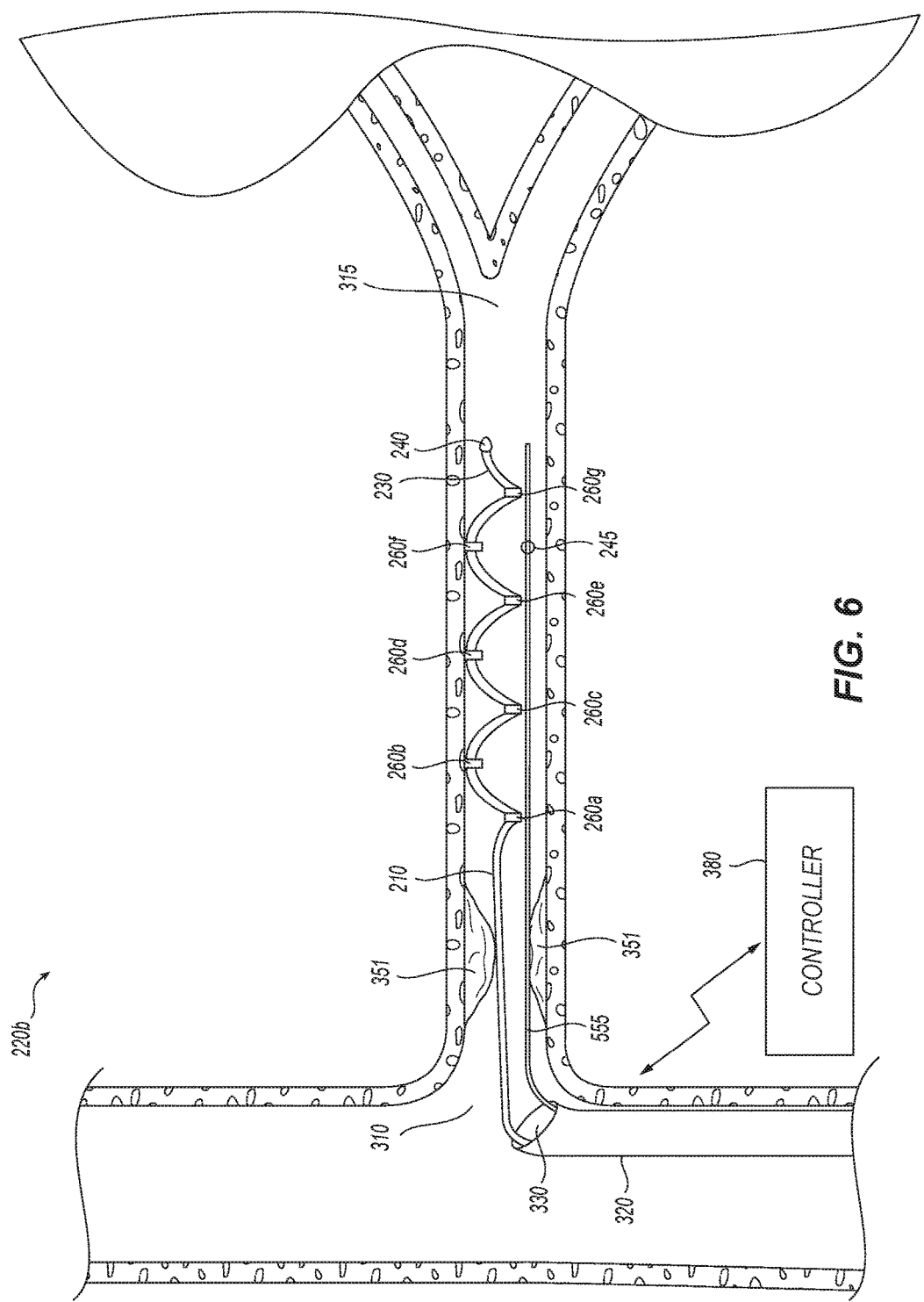
FIG. 6 is a side view of the distal portions of the neuromodulation catheter and the sensing guidewire of FIG. 5 positioned within a blood vessel.

FIG. 6 is a side view of the distal portion of the neuromodulation assembly 230 and guidewire 555 of FIG. 5 positioned within a blood vessel in accordance with an embodiment of the present technology. As mentioned above, the sensor 240 can be coupled to one of the shaft 220 or the guidewire 555 while the transmitter 245 is coupled to the other. As such, the sensor 240 and the transmitter 245 can be delivered independently of each other.

In the illustrated embodiment, the sensor 240 is coupled to shaft 220 and delivered through the guide catheter 320 with the neuromodulation assembly 230 to a first position along the vessel (e.g., renal artery RA). Once catheter 210 is positioned, the guidewire 555 with the transmitter 245 is delivered through the guide catheter 320 to a second position proximate the first position. For purposes of clarity, FIG. 6 shows neuromodulation assembly 230 being not fully deployed within the blood vessel, and guidewire 555 is disposed alongside assembly 230. It is expected that in a typical deployment, neuromodulation assembly 230 is fully deployed within the blood vessel such that each energy delivery element 260 contacts the vessel wall to the extent possible, and guidewire 555 is disposed within assembly 230. The user can activate the sensor 240 to detect one or more hemodynamic parameters at the first position and can activate the transmitter 245 to send the location of the neuromodulation assembly 230 to the receiver 287. As described above with reference to FIGS. 2 and 3, the system 500 identifies whether each energy delivery element 260 is positioned at an identified target region or an identified avoidance region. If an energy delivery element 260 is positioned at an identified target region as illustrated on user interface 297, the user can deliver neuromodulation therapy through that element. If an energy delivery element 260 is positioned near an identified avoidance region (e.g., near a stenosis 351, ostium 310, or bifurcation 315) the user can skip delivering neuromodulation therapy through that element and/or re-position the neuromodulation assembly 230 and the guidewire 555 to identify one or more target regions in the vessel. Alternatively, the user can reposition the transmitter 245 adjacent each of energy delivery elements 260a-g to determine if an energy delivery element 260 is near an identified target region.

As illustrated in FIG. 6, the sensor 240 is located distal to energy delivery element 260g and the transmitter 245 is located substantially adjacent to energy delivery element 260f in the vessel. In other embodiments, the sensor 240 can be located proximal to at least one energy delivery element 260 and the transmitter 245 can be located substantially adjacent to, proximal to, or distal to another energy delivery element 260. In further embodiments, the guidewire 555 can be delivered to a first position in the vessel (e.g., renal artery RA) before the neuromodulation assembly 230. For example, if the CFD model of the patient's vessel was generated before the transmitter 245 was delivered, such as during a previous procedure or as part of a prior positioning, the user may have previously identified a desired target location to deliver neuromodulation therapy. In this embodiment, the user can activate the transmitter 245 to locate the desired target location and position an energy delivery element of the neuromodulation assembly 230 at the desired location.

Figure 7:
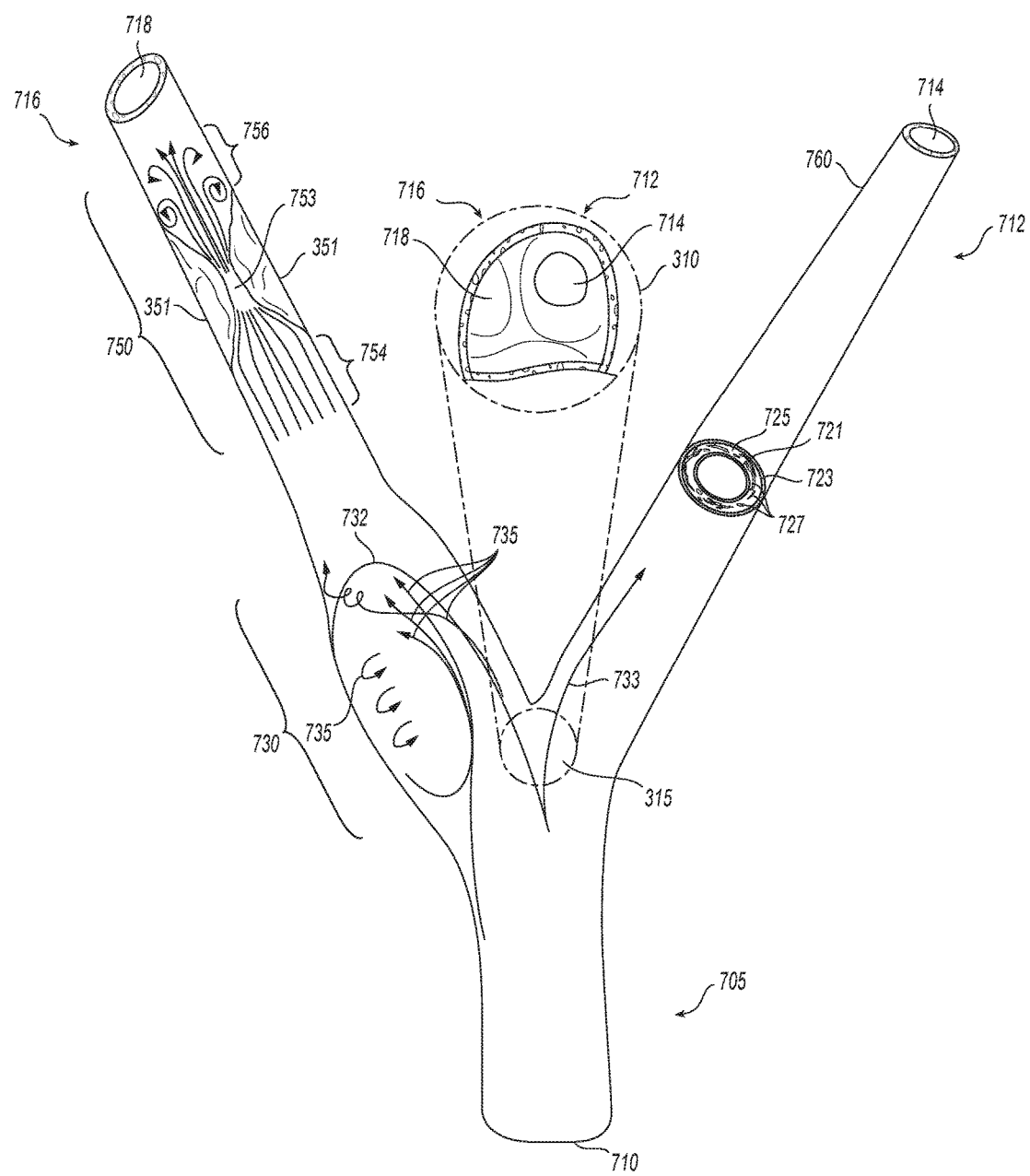
FIGS. 7-9 are anatomic and conceptual side views, cross-sectional views, and enlarged views of a blood vessel illustrating a plurality of physiologic and pathologic features.
Figure 8:
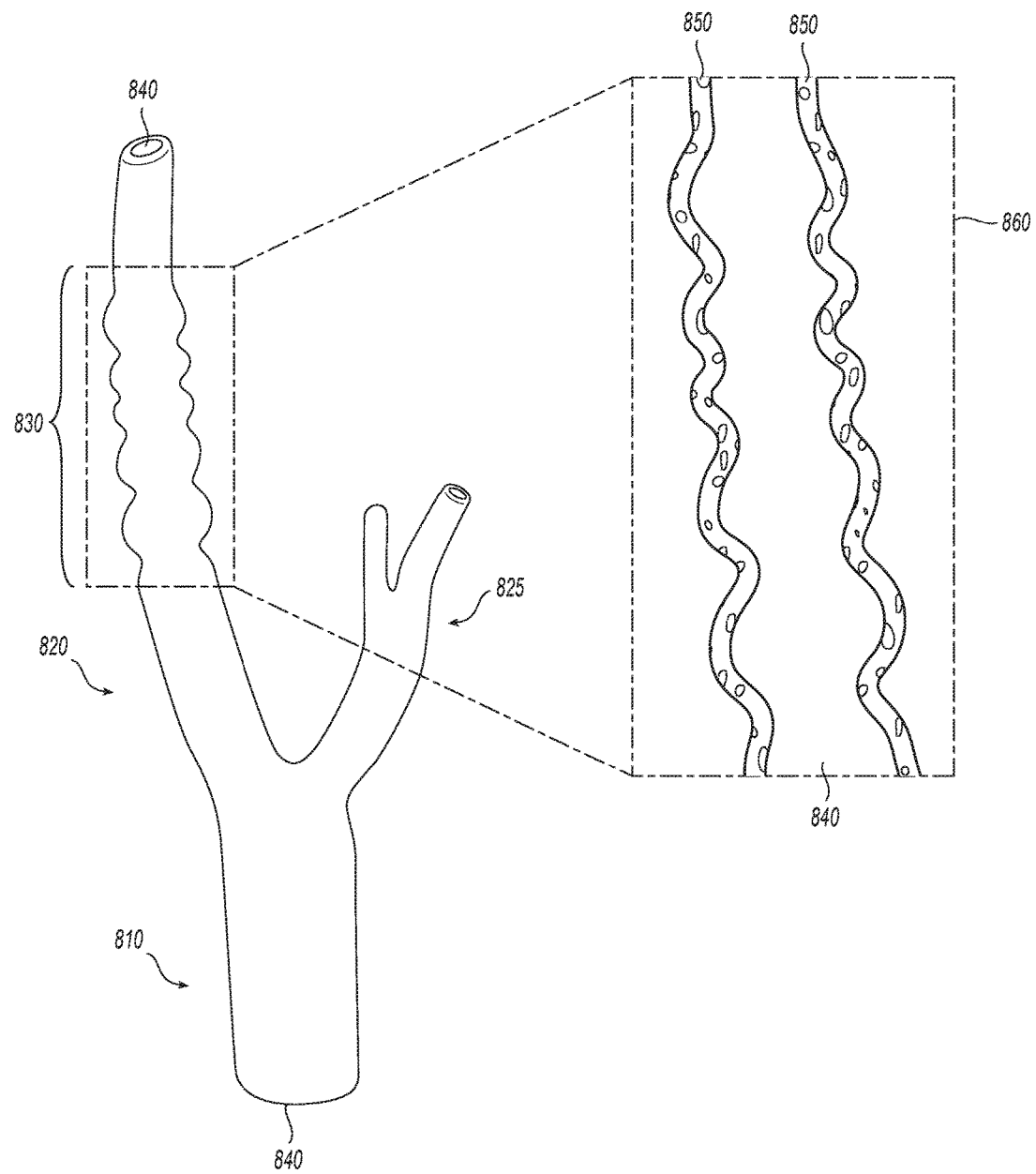
Figure 9:
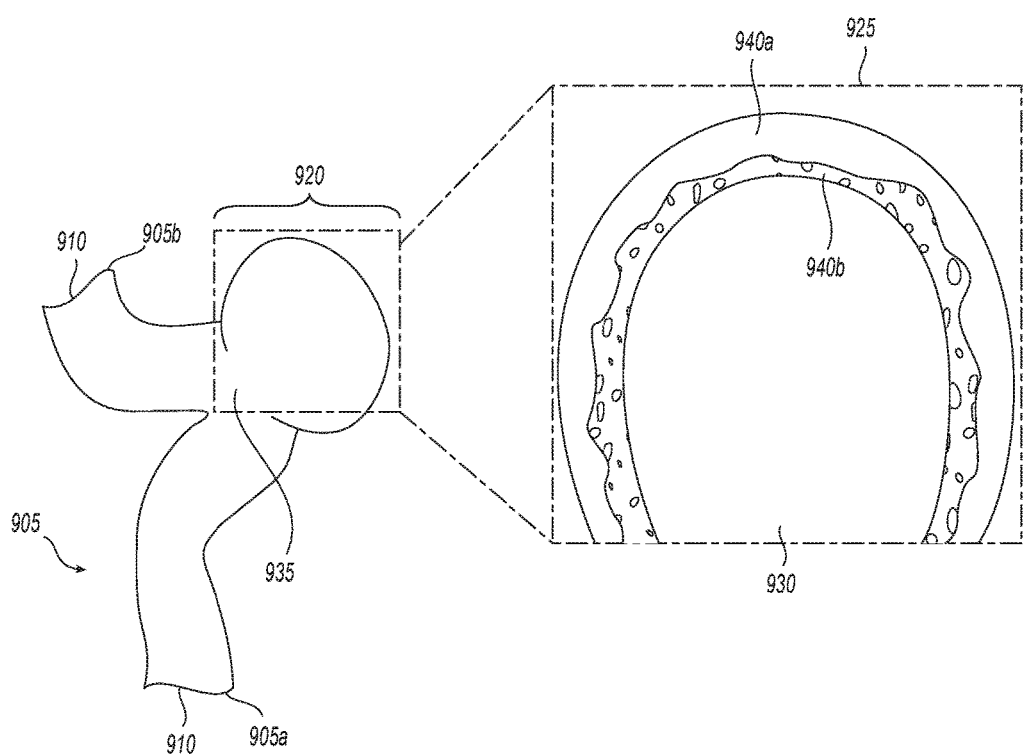

FIGS. 7-9 are anatomic and conceptual side views, cross-sectional views, and exploded views of a blood vessel illustrating a variety of physiologic and pathologic features. Although the configuration of a blood vessel can have many variations and/or a blood vessel can have local flow abnormalities, FIGS. 7-9 are shown for illustrative purposes and are not intended to exaggerate or limit the number, location, configurations and/or local flow abnormalities that may occur in a blood vessel. As discussed above, delivering perivascular neuromodulation therapy to an identified avoidance region (e.g., a certain location with one or more physiologic features, pathologic features, and/or flow abnormalities) may result in an unwanted event. Accordingly, the method 100, systems 200, 500, and embodiments thereof can assist clinicians in avoiding such undesirable regions while also guiding users to desired target regions.

As illustrated in FIG. 7, a main vessel 705 branches at a bifurcation 315 into two branches including a right branch 712 and a left branch 716. At the bifurcation 315, the branched vessels form a carina at the vessel wall (shown in detailed view). A lumen 710 extends through the main vessel 705 and divides into each branch as a right lumen 714 and a left lumen 718. Blood can flow through the lumen 710 and can split at the bifurcation 315 into right flow 733 and left flow 732. Through linear (e.g., straight) portions of the vessel having a healthy lumen (e.g., a smooth wall and a normal inner diameter to allow blood to flow without disturbance), blood flow is often laminar and imparts physiologic shear stress (e.g., hemodynamic stress) on the vessel wall. Such wall shear stress (WSS) can be measured as force per unit area exerted on the vessel wall and can be affected by blood viscosity and blood flow. Physiologic (e.g., healthy) WSS is about 1 to about 7 dynes/cm$^2$ in the venous system and about 10 to about 15 dynes/cm$^2$ in the arterial system. The split flow into the right branch 712 and the left branch 716 places relatively high wall shear stress (HWSS) of about 27 dynes/cm$^2$ or greater on the vessel wall at the bifurcation 315. For example, abrupt geometric changes in the vessel wall, such as the bifurcation 315, are subject to HWSS. Furthermore, when flow trajectories change and blood contacts the vessel wall in a non-laminar manner, the blood flow can become turbulent and/or form eddy currents 735 as illustrated in region 730 of FIG. 7. For example, eddy currents 735 can reduce normal wall shear stress to a relatively low wall shear stress (LWSS), such as about 12.6 dynes/cm$^2$ or less. These areas of LWSS often occur distal to abrupt geometric changes (e.g., bifurcation 315) and/or adjacent to areas of HWSS. In addition, wall shear stress at a certain location in the vessel can vary, for example, having both HWSS and LWSS at a portion of the vessel (i.e., at the bifurcation 315 or a tapered region 760).

In addition to the above physiologic changes in vascular geometry, blood flow can also be altered by pathological events, such as changes in the vessel wall. For example, portions of the vessel wall that have thickened such as at a stenosis 351 impinge the laminar flow 754 in region 750. As illustrated, the left lumen 718 narrows at stenosis 351, resulting in laminar flow 754 becoming turbulent flow 756 along the distal portion of the region of impinged flow 750. Vascular calcification 720 occurs by formation and/or deposit of calcium 727 in the vessel wall. While calcium deposits can be located in the intima 721 and/or adventitia 723, deposits are most commonly found in the media 725. A portion of the vessel wall having a calcification 720 (e.g., calcium deposits) is less elastic, having an impaired ability to respond to changes in blood flow, blood pressure, etc. compared to a non-calcified region.

As illustrated in FIGS. 8 and 9, the vessel wall can have other diseases that can result in an unwanted event in response to delivery of neuromodulation therapy. For example, FIG. 8 illustrates a main vessel 810 which branches into a left branch 820 and a right branch 825 having fibromuscular dysplasia in region 830. A lumen 840 extends from the main vessel 810 into the left branch 820 and through the region 830 having fibromuscular dysplasia. Referring to enlarged sectional view 860, fibromuscular dysplasia causes abnormal thickening of the vessel walls 850. While not intending to be limiting, FIG. 8 illustrates multi-focal type fibromuscular dysplasia, as distinguished from focal and adventitial types. Fibromuscular dysplasia can affect many different vessels; however the most common vessels include carotid arteries, vertebral arteries, renal arteries, and arteries coupled to arms, legs, and intestines.

The vessel wall can also be altered by the formation of an aneurysm, which is a localized dilation or ballooning of the vessel wall that may be associated with hypertension and/or may occur at weak portions of the vessel wall. Aneurysms are often classified by their location, for example, arterial, venous, cardiac, coronary, aorta, brain, legs, kidneys, and capillaries. As illustrated in FIG. 9, main vessel 905 has a lumen 910 extending from a proximal portion 905a through a distal portion 905b. An aneurysm 920 is located between the proximal portion 905a and the distal portion 905b. Referring to enlarged sectional view 925, the aneurysm 920 includes a large lumen 930 (e.g., extending from the lumen 910), an outer wall 940a, and an inner wall 940b. While not intending to be limiting, FIG. 9 illustrates a saccular aneurysm 920, one of several types of aneurysms including fusiform and microaneurysms.

Figure 10:
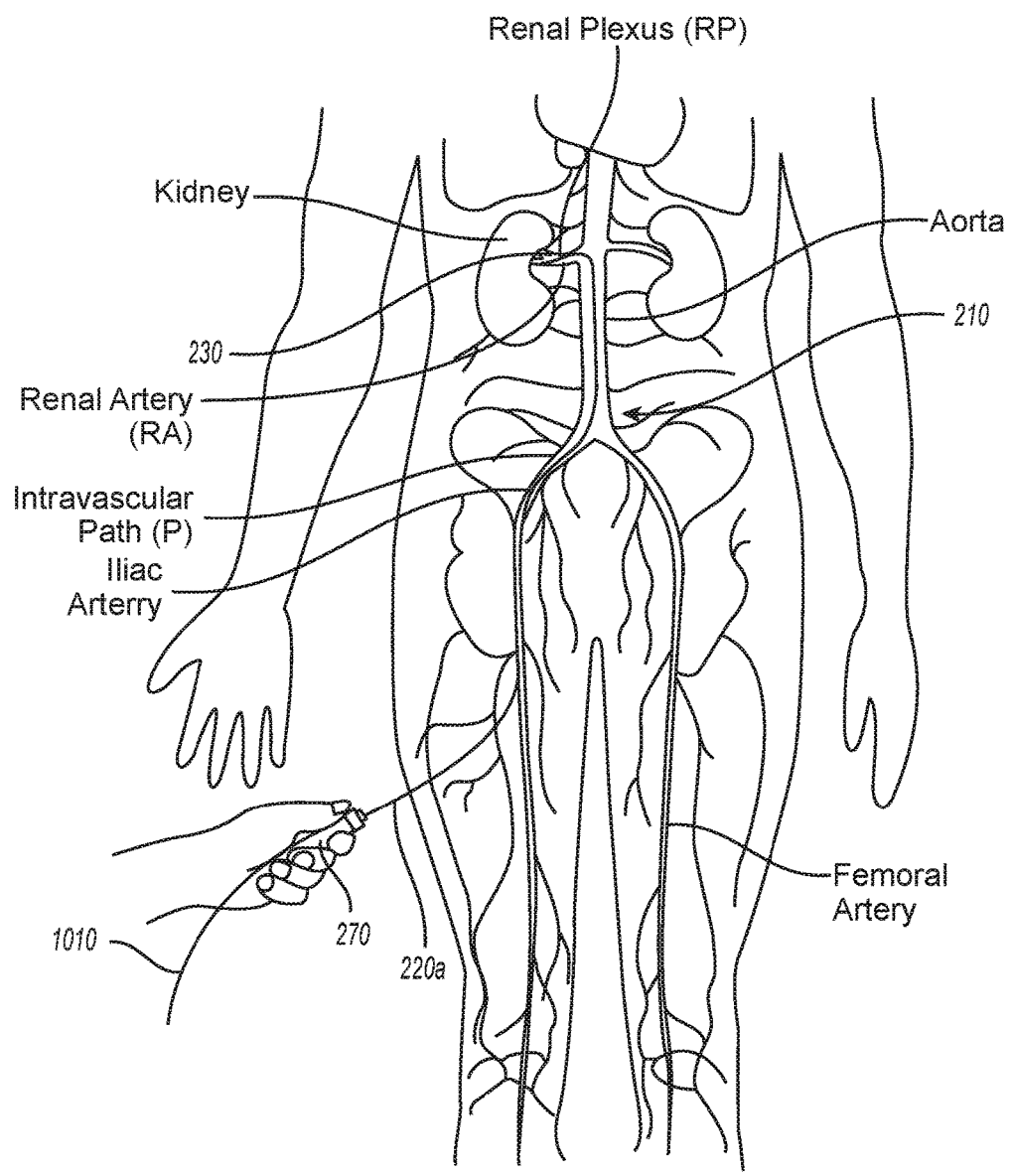
FIG. 10 illustrates modulating renal nerves with a neuromodulation catheter described herein in accordance with an additional embodiment of the present technology.

FIG. 10 (with additional reference to FIGS. 2-6) illustrates modulating renal nerves with a neuromodulation catheter described herein in accordance with an additional embodiment of the present technology. The neuromodulation catheter 210 provides access to the renal plexus RP through an intravascular path P, such as a percutaneous access region in the femoral (illustrated), brachial, radial, or axillary artery to a targeted treatment region within a respective renal artery RA. By manipulating the proximal portion 220a of the shaft 220 from outside the intravascular path P, a clinician may advance the shaft 220 through the sometimes tortuous intravascular path P and remotely manipulate the distal portion 220b (FIGS. 2-6) of the shaft 220. In the embodiment illustrated in FIG. 10, the neuromodulation assembly 230 is delivered intravascularly to the treatment region using a guidewire 1010 in an OTW technique. At the treatment region, the guidewire 1010 can be at least partially withdrawn or removed, and the neuromodulation assembly 230 can transform or otherwise be moved to a deployed arrangement for delivering energy at the treatment region. In other embodiments, the neuromodulation assembly 230 may be delivered to the treatment region within a guide sheath (not shown) with or without using the guidewire 1010. When the neuromodulation assembly 230 is at the target region, the guide sheath, if used, may be at least partially withdrawn or retracted such that the neuromodulation assembly 230 can transform into the deployed configuration. In still other embodiments, the shaft 220 itself may be steerable such that the neuromodulation assembly 230 may be delivered to the treatment region without the aid of the guidewire 1010 and/or a guide sheath.

In addition to the method 100, systems 200, 500, and embodiments thereof described herein regarding assessing hemodynamics for optimizing delivery of neuromodulation therapy, image guidance, e.g., computed tomography (CT), fluoroscopy, intravascular ultrasound (IVUS), optical coherence tomography (OCT), intracardiac echocardiography (ICE), or another suitable guidance modality, or combinations thereof, may also aid the clinician's positioning and manipulation of the neuromodulation catheter 210 in accordance with the present technology. For example, a fluoroscopy system (e.g., including a flat-panel detector, x-ray, or c-arm) can be rotated to accurately visualize and identify the target treatment region. In other embodiments, the treatment region can be determined using IVUS, OCT, and/or other suitable image mapping modalities that can correlate the target treatment region with an identifiable anatomical structure (e.g., a spinal feature) and/or a radiopaque ruler (e.g., positioned under or on the patient) before delivering the neuromodulation assembly 230. Further, in some embodiments, image guidance components (e.g., IVUS, OCT) may be integrated with the neuromodulation catheter 210 and/or run in parallel with the neuromodulation catheter 210 to provide image guidance during positioning of the neuromodulation assembly 230. For example, image guidance components (e.g., IVUS or OCT) can be coupled to the neuromodulation assembly 230 to provide three-dimensional images of the vasculature proximate the target region to facilitate positioning or deploying the neuromodulation assembly 230 within the target vessel. As described above, the method 100, systems 200, 500, and embodiments thereof can include determining the location of avoidance regions and/or target regions for delivering neuromodulation therapy and transmitting location information to the user. The image guidance modalities described herein can be used in conjunction with methods, systems, and embodiments of the present technology to provide location information of the neuromodulation catheter 210 to the user in real-time.

Energy from the electrodes 260 (FIGS. 2-6) and/or other energy delivery elements may then be applied to identified target tissue to induce one or more desired neuromodulating effects on localized regions of the renal artery RA and adjacent perivascular regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery elements and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

Hypothermic effects may also provide neuromodulation. For example, a cryotherapeutic applicator may be used to cool tissue at a target region to provide therapeutically-effective direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Embodiments of the present technology can include cooling a structure at or near an inner surface of a renal artery wall such that proximate (e.g., adjacent) tissue is effectively cooled to a depth where sympathetic renal nerves reside. For example, the cooling structure is cooled to the extent that it causes therapeutically effective, cryogenic renal-nerve modulation. Sufficiently cooling at least a portion of a sympathetic renal nerve is expected to slow or potentially block conduction of neural signals to produce a prolonged or permanent reduction in renal sympathetic activity.

Figure 11:
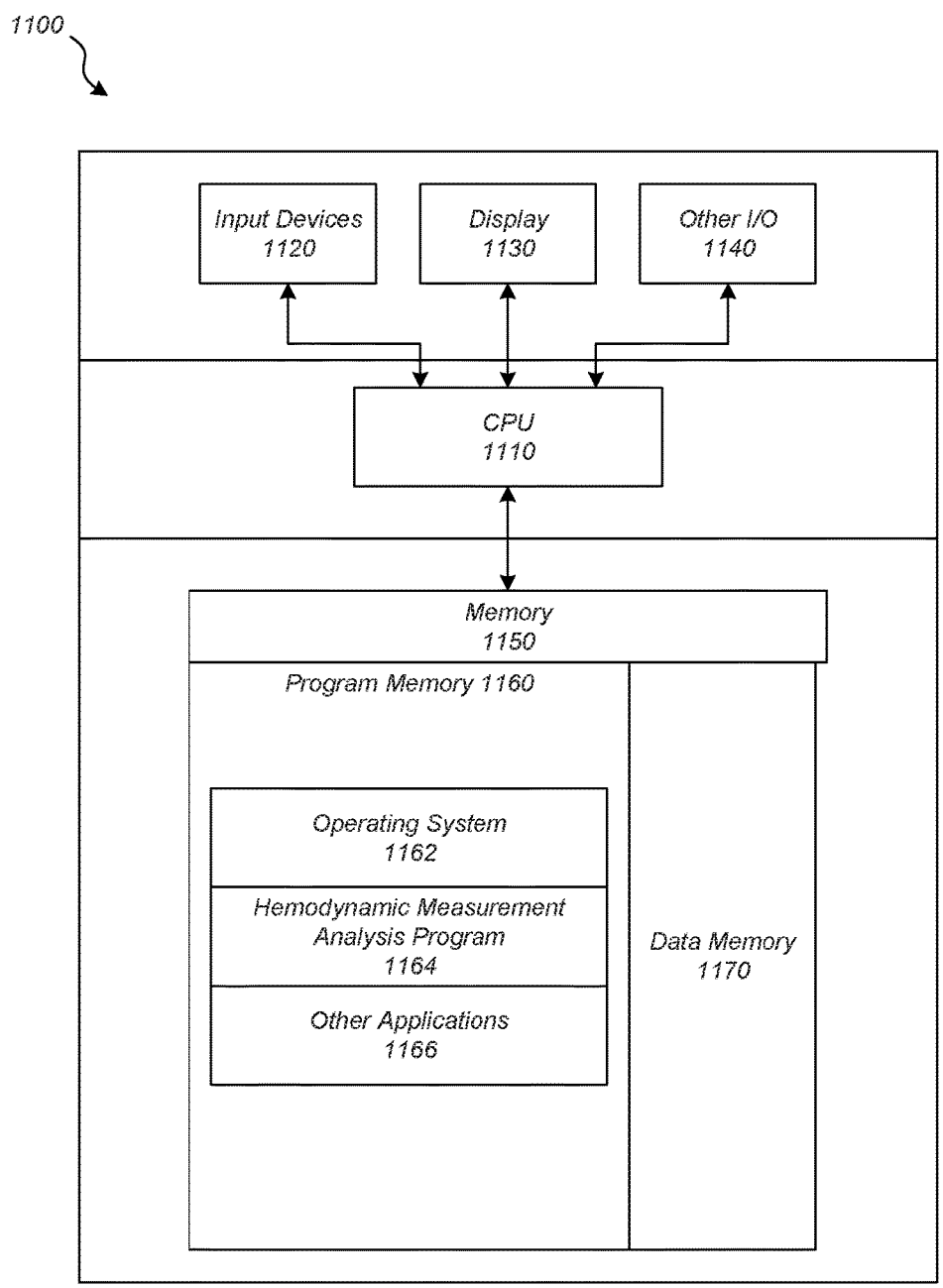
FIG. 11 is a block diagram illustrating an overview of devices on which some implementations of the present technology may operate.

As illustrated in FIG. 11, at least a portion of the CFD model can be generated using systems 200 and 500, device 1100, and environment 1200 described below in accordance with the present technology. For example, the CFD workflow can, in part, be performed by computer 1110 configured to execute instructions (e.g., one or more than one software applications 1164 and 1166 for facilitating operation of the CFD workflow) for generating the CFD model. In some embodiments, the CFD model can be saved to and/or stored at one or more servers 1220 (e.g., a central server) with reference to FIG. 12.

FIG. 11 is a block diagram illustrating an overview of devices on which some implementations of the present technology can operate. The devices can comprise hardware components of a device 1100 for analyzing the patient's imaging data and hemodynamic parameters, comparing one or more of the patient's hemodynamic parameters and/or optimized parameters against a threshold hemodynamic parameter, and providing a recommendation of whether to deliver neuromodulation therapy at a location in a vessel. The device 1100, for example, can be incorporated into the console 295 described above with respect to FIG. 2.

The device 1100 can include, for example, one or more input devices 1120 providing input to a central processing unit ("CPU"; processor) 1110, notifying the CPU 1110 of actions. The actions are typically mediated by a hardware controller that interprets the signals received from the input device and communicates the information to the CPU 1110 using a communication protocol. The input devices 1120 include, for example, a receiver for receiving signals from a monitoring device (e.g., the sensor 240 and/or the transmitter 245 described with reference to FIGS. 2-6), a mouse, a keyboard, a touchscreen, an infrared sensor, a touchpad, a wearable input device, a camera- or image-based input device, a microphone, and/or other user input devices.

The CPU 1110 can be a single processing unit or multiple processing units in a device or distributed across multiple devices. CPU 1110 can be coupled to other hardware devices, for example, with the use of a bus, such as a PCI bus or SCSI bus. The CPU 1110 can communicate with a hardware controller for devices, such as a display 1130. The display 1130, which can be the display 297 of the console 295 (FIG. 2), can be used to display text and graphics. In some examples, the display 1130 provides graphical and textual visual information to the user, such as information related to one or more of the patient's hemodynamic parameters (e.g., individual and compared to threshold hemodynamic parameters), a summary of data detected by one or more sensors 240 and/or transmitters 245 coupled to the device 1100, and/or other suitable information. In some implementations, the display 1130 includes the input device as part of the display, such as when the input device is a touchscreen or is equipped with an eye direction monitoring system. In some implementations, the display 1130 is separate from the input device 1120. Examples of display devices are: an LCD display screen, an LED display screen, a projected, holographic, or augmented reality display (such as a heads-up display device or a head-mounted device), and so on. Other input/output (I/O) devices 1140 can also be coupled to the processor, such as a network card, video card, audio card, USB, firewire or other external device, camera, printer, speakers, CD-ROM drive, DVD drive, disk drive, or Blu-Ray device.

In some implementations, the device 1100 also includes a communication device capable of communicating wirelessly or wire-based with a network node. The communication device can communicate with another device or a server through a network using, for example, TCP/IP protocols. Device 1100 can utilize the communication device to distribute operations across multiple network devices.

The device 1100 can execute embodiments of blocks 110, 120, 130, 140 and 150 of method 100 described above with respect to FIG. 1. In order to execute these embodiments, the CPU 1110 can be configured to have access to a memory 1150. A memory includes one or more of various hardware devices for volatile and non-volatile storage, and can include both read-only and writable memory. For example, a memory 1150 can include random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. The memory 1150 can include program memory 1160 for storing programs and software, such as an operating system 1162, a hemodynamic parameter analysis program 1164, and other application programs 1166. The hemodynamic parameter analysis program 1164, for example, can include one or more algorithms for analyzing various indices related to one or more hemodynamic parameters, providing a hemodynamic parameter summary or report, or other information related to delivering neuromodulation therapy to the patient based on hemodynamic parameters. The memory 1150 can also include data memory 1170 including sensed and/or recorded data from one or more of the sensors, patient data, algorithms related to hemodynamic parameter analysis, configuration data, settings, user options or preferences, etc., which can be provided to the program memory 1160 or any element of the device 1100.

Some implementations can be operational with numerous other general purpose or special purpose computing system environments or configurations. Examples of well-known computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, set-top boxes, programmable consumer electronics, network PCs, minicomputers, mainframe computers, distributed computing environments that include any of the above systems or devices, or the like.

Figure 12:
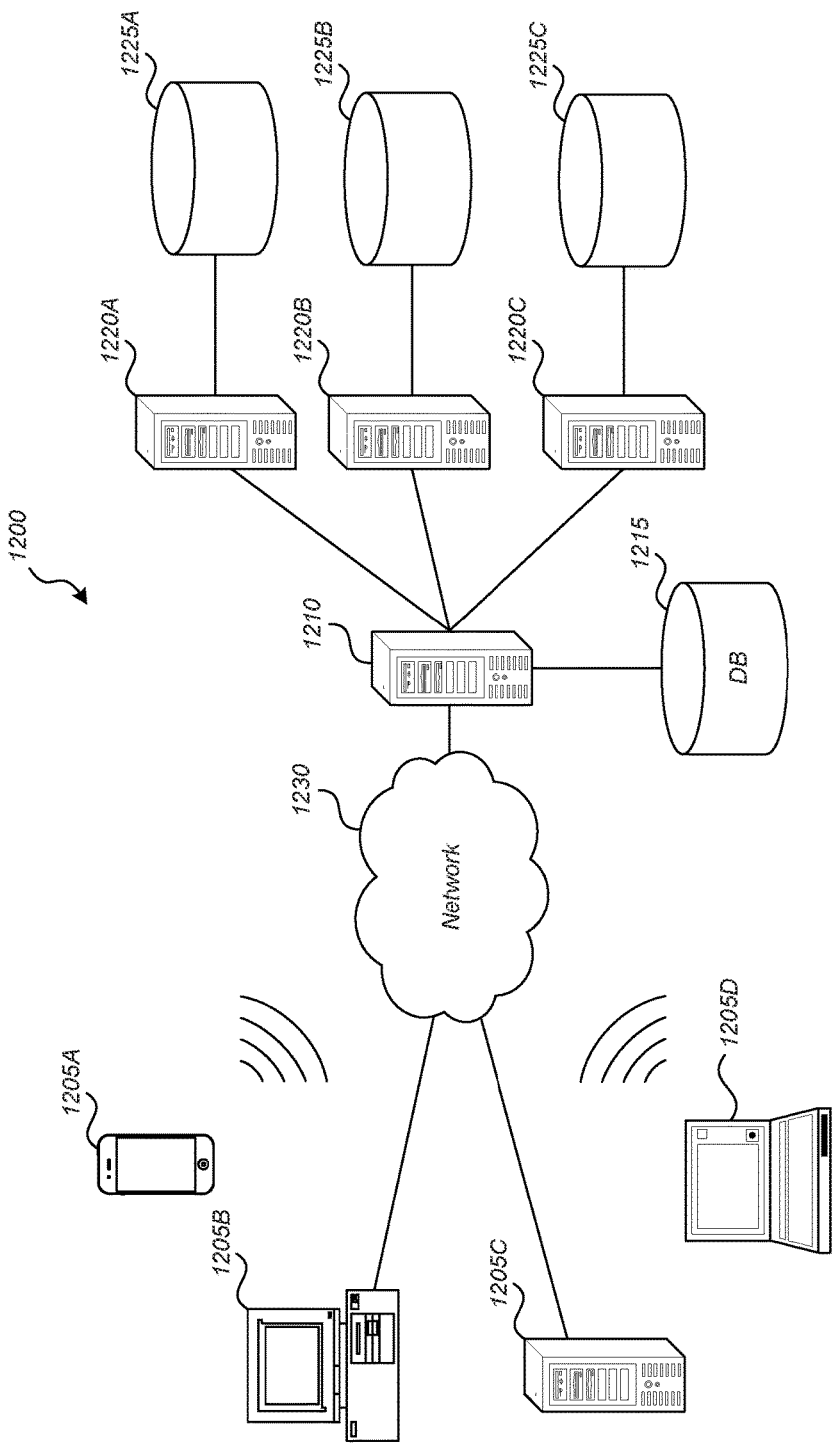
FIG. 12 is a block diagram illustrating an overview of an environment in which some implementations of the present technology may operate.

FIG. 12 is a block diagram illustrating an overview of an environment 1200 in which some implementations of the disclosed technology can operate. The environment 1200 can include one or more client computing devices 1205A-D (identified collectively as "client computing devices 1205"), examples of which can include the device 1100 of FIG. 11. The client computing devices 1205 can operate in a networked environment using logical connections through a network 1230 to one or more remote computers, such as a server computing device 1210.

In some implementations, server 1210 can be an edge server that receives client requests and coordinates fulfillment of those requests through other servers, such as servers 1220A-C. The server computing devices (not shown) can comprise computing systems, such as device 1100 (FIG. 11). Though each server computing device (not shown) can logically be a single server, the server computing devices (not shown) can each be a distributed computing environment encompassing multiple computing devices located at the same or at geographically disparate physical locations. In some implementations, each server 1220 corresponds to a group of servers.

The client computing devices 1205 and the server computing devices 1210 and 1220 can each act as a server or client to other server/client devices. The server 1210 can connect to a database 1215. The servers 1220A-C can each connect to corresponding databases 1225A-C. As discussed above, each server 1220 can correspond to a group of servers, and each of these servers can share a database or can have their own database. The databases 1215 and 1225 can warehouse (e.g., store) information such as raw data (e.g., related to patient hemodynamic parameters, three-dimensional representations, CFD representations, representations), algorithms (e.g., deriving hemodynamic parameters, digital three-dimensional representations, CFD representations, representations), other patient information, and/or other information necessary for the implementation of the systems and methods described above with respect to FIGS. 1-11. Though the databases 1215 and 1225 are displayed logically as single units, the databases 1215 and 1225 can each be a distributed computing environment encompassing multiple computing devices, can be located within their corresponding server, or can be located at the same or at geographically disparate physical locations.

The network 1230 can be a local area network (LAN) or a wide area network (WAN), but can also be other wired or wireless networks. The network 1230 may be the Internet or some other public or private network. The client computing devices 1205 can be connected to the network 1230 through a network interface, such as by wired or wireless communication. While the connections between the server 1210 and servers 1220 are shown as separate connections, these connections can be any kind of local, wide area, wired, or wireless network, including the network 1230 or a separate public or private network.

III. Renal Neuromodulation

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable target regions during a treatment procedure. The target region can be within or otherwise proximate to a renal lumen (e.g., a renal artery, a ureter, a renal pelvis, a major renal calyx, a minor renal calyx, or another suitable structure), and the treated tissue can include perivascular tissue (at least proximate to a wall of the renal lumen). For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a target region in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed electrical energy, microwave energy, optical energy, focused ultrasound energy (e.g., high-intensity focused ultrasound energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular or intraluminal), optical coherence tomography, or another suitable imaging modality). For example, imaging can be used to identify an anatomical position of a treatment location (e.g., as a set of coordinates relative to a reference point). The coordinates can then be entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 70° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 40° C. (e.g., less than about 95° C., less than about 90° C., or less than about 85° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., microneedles) that can be retracted or otherwise blocked before deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

IV. Related Anatomy and Physiology

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 13:
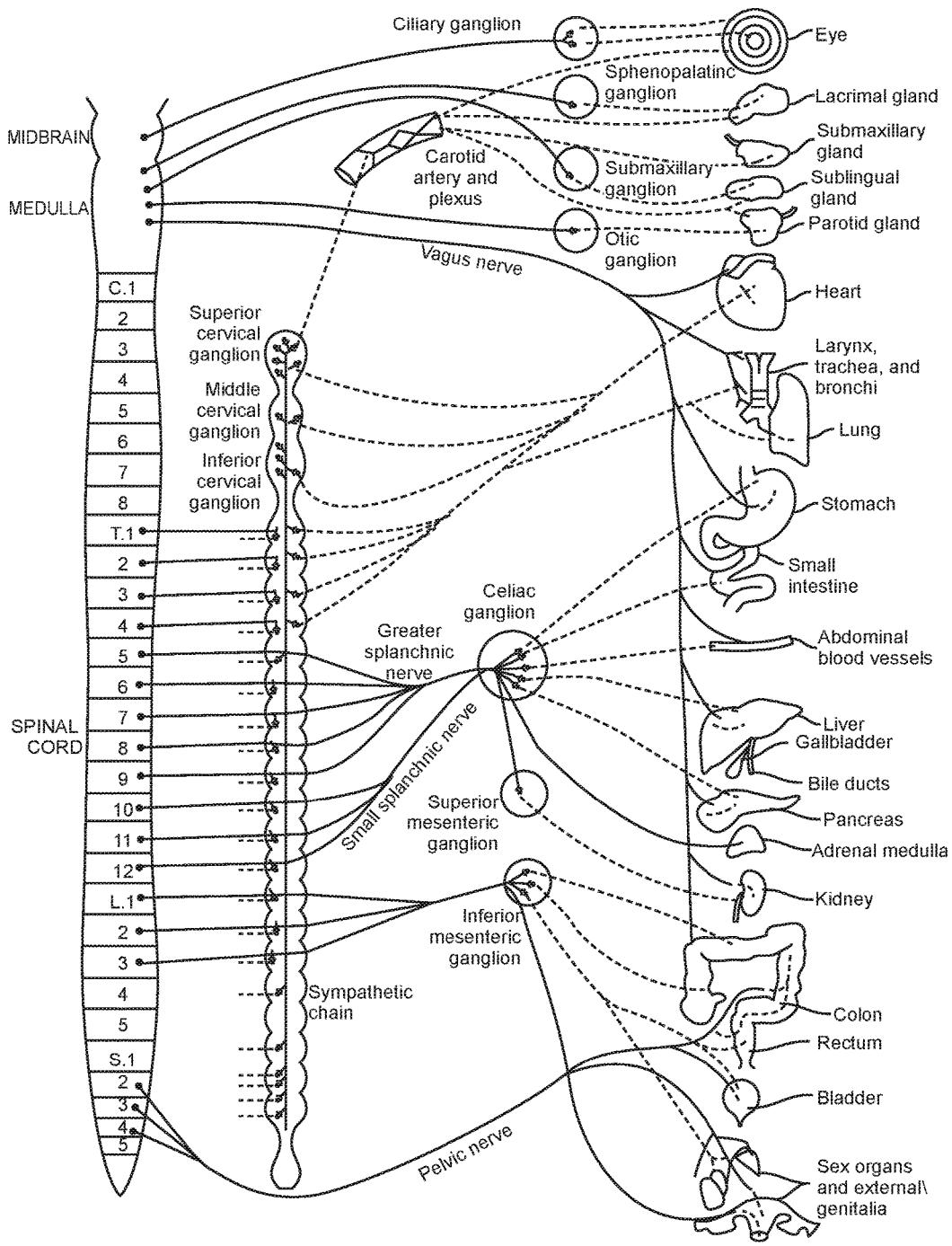
FIG. 13 is a conceptual illustration of the sympathetic nervous system (SNS) and how the brain communicates with the body via the SNS.

As shown in FIG. 13, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at regions called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 14:
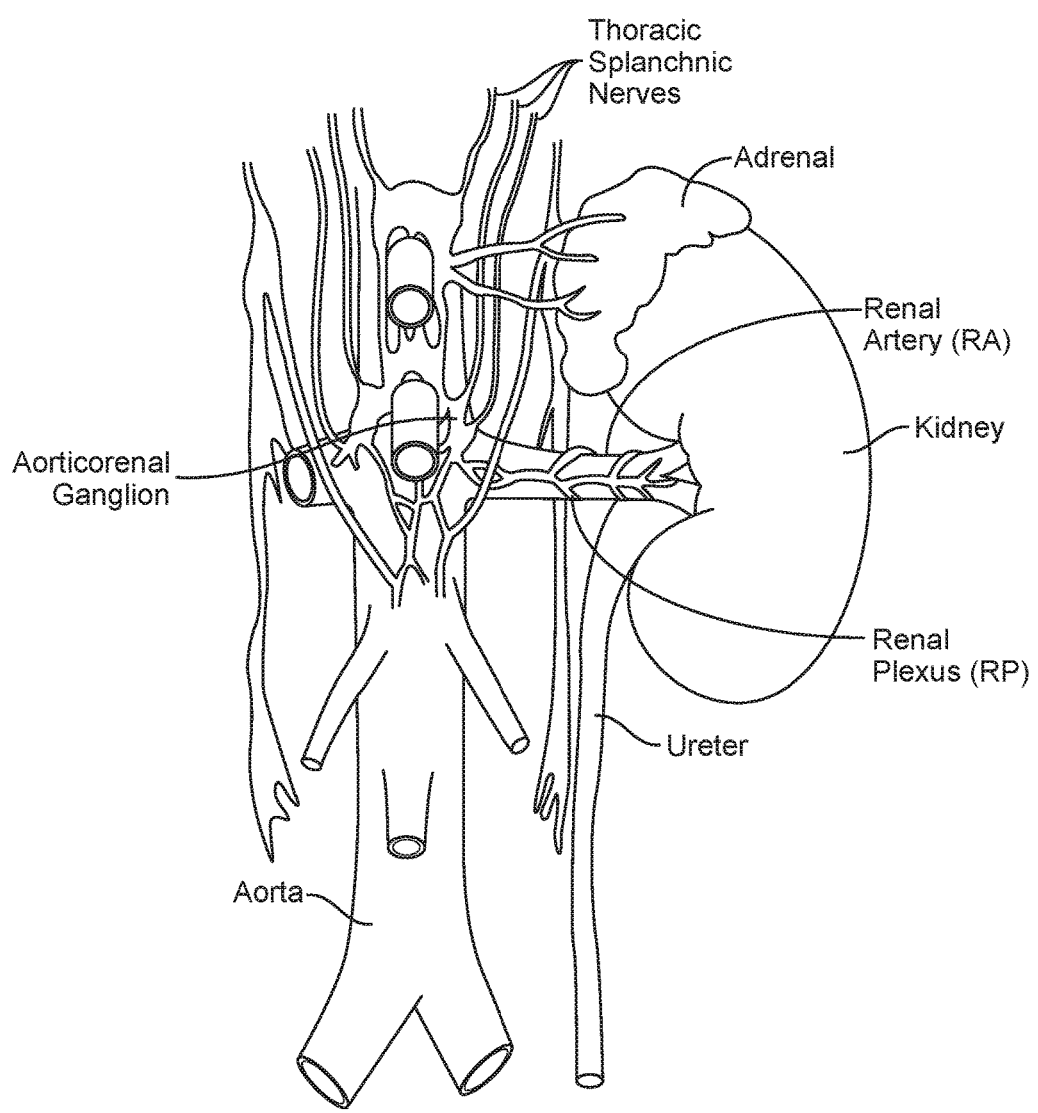
FIG. 14 is an enlarged anatomic view of nerves innervating a left kidney to form the renal plexus surrounding the left renal artery.

As FIG. 14 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure, and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic overactivity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 15:
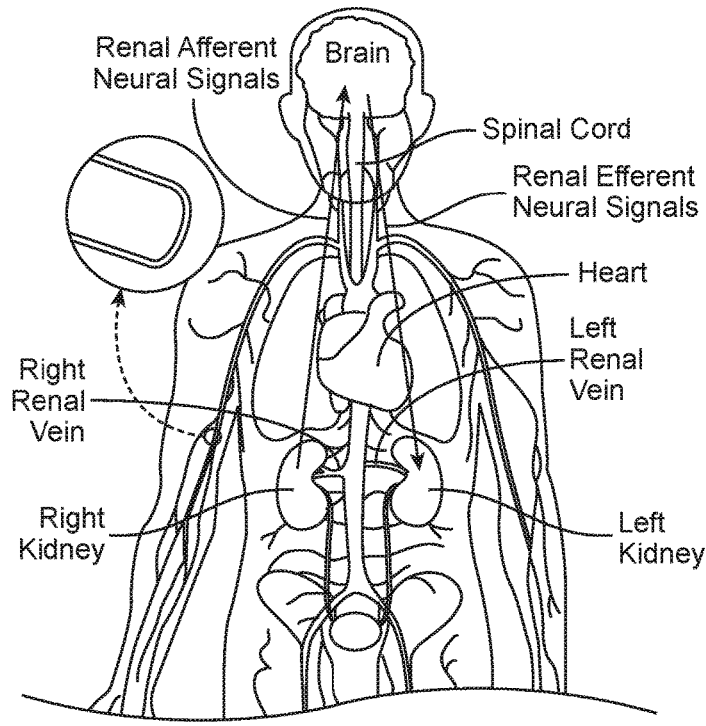
FIGS. 15 and 16 are anatomic and conceptual views, respectively, of a human body depicting neural efferent and afferent communication between the brain and kidneys.
Figure 16:
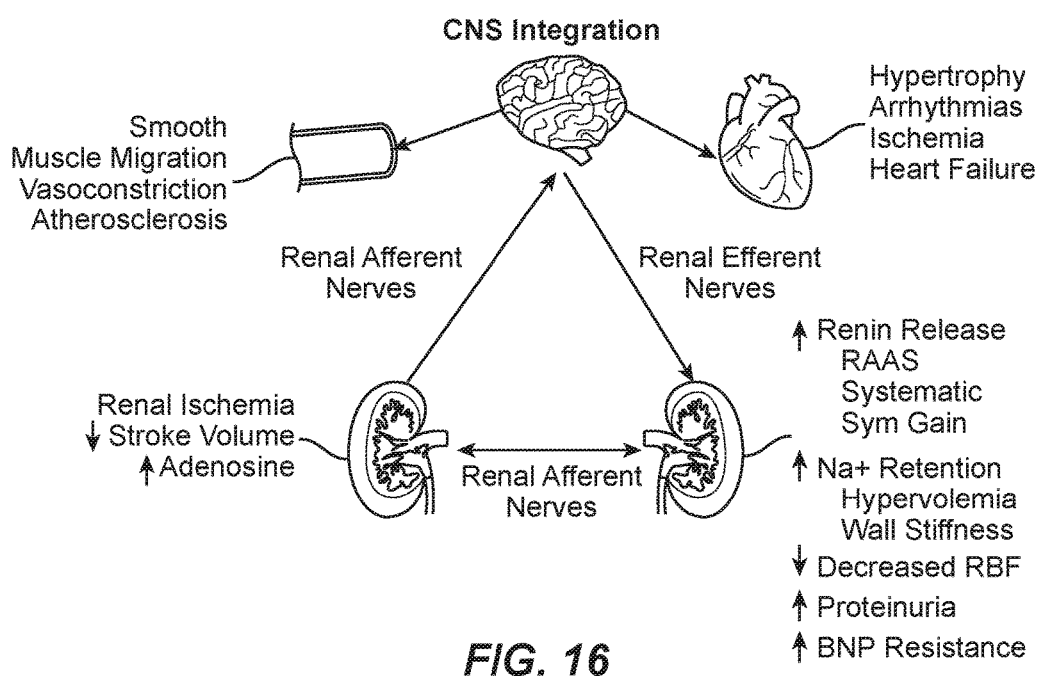

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 15 and 16, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic overactivity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 13. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down-regulation of sympathetic drive that accompanies renal denervation.

C. Achieving Intravascular Access to the Renal Artery

Figure 17:
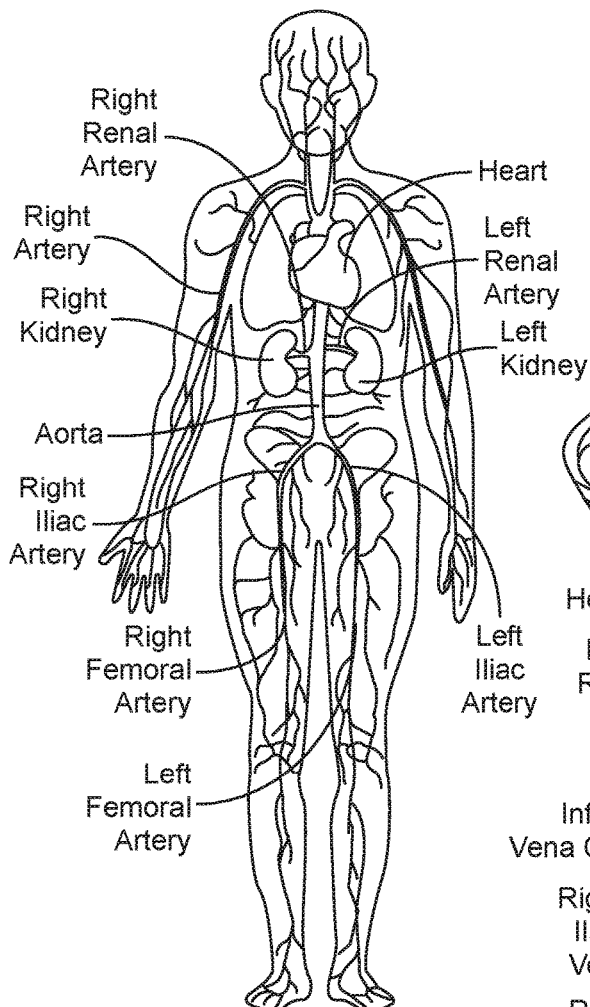
FIGS. 17 and 18 are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 17 shows, blood moved by contractions of the heart is conveyed from the left ventricle of the heart by the aorta. The aorta descends through the thorax and has branches into the left and right renal arteries. Below the renal arteries, the aorta bifurcates at the left and right iliac arteries. The left and right iliac arteries descend, respectively, through the left and right legs and join the left and right femoral arteries.

Figure 18:
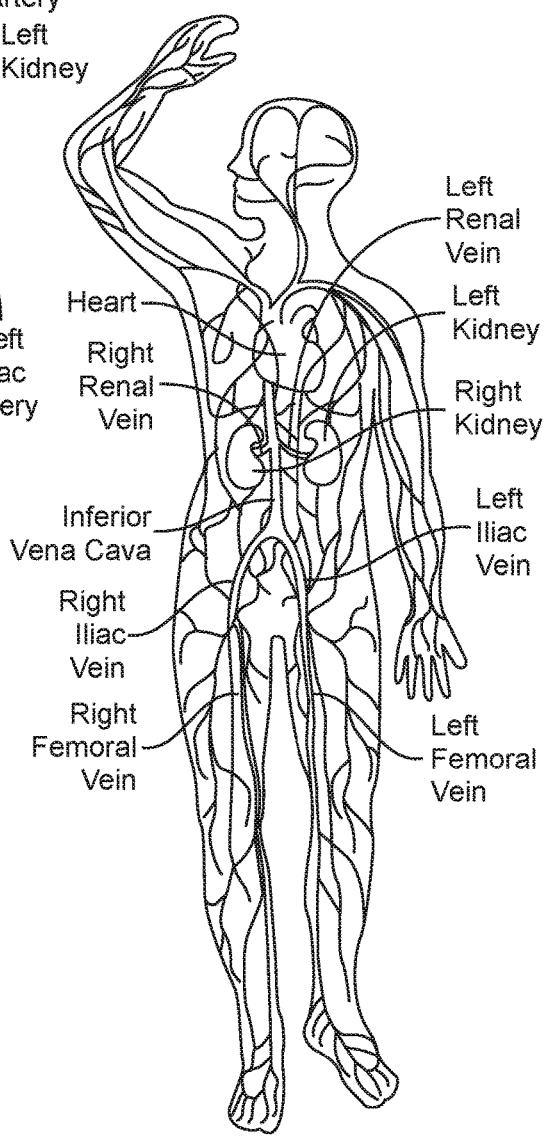

As FIG. 18 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access region, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/ mechanical, spatial, fluid dynamic/hemodynamic, and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems, and methods for achieving renal neuromodulation via intravascular access, should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between the neuromodulatory apparatus and a luminal surface of the artery, nerves in and around the adventitia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment region, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

V. Additional Examples

The following examples are illustrative of several embodiments of the present technology:

1. A method for evaluating a vessel for neuromodulation therapy, the method comprising:
receiving, at a processor, digital data regarding three-dimensional imaging of the vessel;
receiving, at the processor, hemodynamic data;
generating, at the processor, a computational fluid dynamics (CFD) model of the vessel based at least in part on the imaging data and the hemodynamic data;
identifying, with reference to the CFD model, avoidance regions of the vessel for neuromodulation therapy, wherein the avoidance regions include regions of at least one of flow separation, eddy formation, flow impingement, low wall shear stress (WSS), or high WSS gradients; and
displaying, on a user interface, a representation of the vessel including visual markers indicating the avoidance regions.

2. The method of example 1 wherein receiving the three-dimensional imaging data includes receiving three-dimensional imaging data of a renal artery, a pulmonary artery, a hepatic artery, a coronary artery, or an aorta.

3. The method of examples 1 or 2 wherein receiving the three-dimensional imaging data of the vessel includes receiving three-dimensional imaging data of a main vessel, at least one branch vessel of the main vessel, or at least one accessory vessel directly coupled to the at least one of the branch vessel or another vessel coupled to the main vessel.

4. The method of any one of examples 1-3, further comprising:

receiving location data from a neuromodulation catheter regarding the position of the neuromodulation catheter in the vessel; and providing, via the processor, a recommendation to a user of whether to proceed with neuromodulation therapy at the device position based on the identified avoidance regions.

5. The method of any one of examples 1-4 wherein providing the recommendation via the processor comprises generating a signal to the user indicative of the avoidance regions, wherein the signal includes an audio signal, a visual signal, a tactile signal, or a combination thereof.

6. The method of any one of examples 1-5 wherein displaying the representation of the vessel further comprises displaying indicators of optimal portions or acceptable portions of the vessel for delivering neuromodulation therapy.

7. The method of any one of examples 1-6 wherein displaying the representation of the vessel further comprises:

displaying a first portion of the vessel on the representation; and displaying a second portion of the vessel on the representation, wherein the second portion corresponds to one or more avoidance regions of the vessel, and wherein the displayed first portion has a lower resolution compared to the displayed second portion.

8. The method of any one of examples 1-7 wherein receiving the hemodynamic data comprises receiving blood pressure data, blood flow data, blood impedance data, or a combination thereof.

9. The method of any one of examples 1-8 wherein receiving the hemodynamic data comprises receiving the pressure data and/or blood flow data via a guidewire having a pressure sensor and/or a flow sensor.

10. The method of any one of examples 1-9 wherein receiving the hemodynamic data comprises:

receiving blood pressure data via an external pressure cuff; and/or receiving blood flow data via magnetic resonance imaging (MRI), ultrasound Doppler shift flow meter, or a combination thereof.

11. The method of any one of examples 1-10 wherein receiving the digital data regarding three-dimensional imaging of the vessel comprises receiving data acquired using angiography, x-ray, computed tomography (CT), MM, or a combination thereof.

12. The method of any one of examples 1-11 wherein receiving hemodynamic data comprises receiving blood pressure data and/or blood flow data measured at a position within a main portion of the vessel having at least generally laminar flow.

13. The method of any one of examples 1-12 wherein receiving hemodynamic data comprises receiving blood pressure data and/or blood flow data measured at a position within at least one branch vessel and/or at least one accessory vessel.

14. The method of any one of examples 1-13 wherein providing the recommendation further comprises:

recommending avoiding neuromodulation therapy at one or more portions of the vessel having at least one hemodynamic parameter in the hemodynamic data that exceeds a threshold hemodynamic parameter, and thereby indicates at least one local flow abnormality.

15. The method of any one of examples 1-14 wherein identifying avoidance regions of the vessel comprises identifying portions of the vessel at or proximate to an ostium, a carina, a taper region, a calcification, a fibromuscular dysplasia, an aneurysm, a bifurcation, or a combination thereof.

16. The method of any one of examples 1-15 wherein generating the computational fluid dynamic model of the vessel comprises applying a hemodynamic parameter derived from empirical data or conglomerate data.

17. A method of identifying a target neuromodulation therapy region in a vessel of a human patient, the method comprising:

receiving, at a processor, digital data regarding three-dimensional imaging of the vessel;

receiving, at the processor, hemodynamic data related to the vessel;

generating, at the processor, a computational fluid dynamics (CFD) representation of the vessel based at least in part on the imaging data and the hemodynamic data, the computational fluid dynamics representation including flow parameters;

identifying, via the processor, target regions of the vessel suitable for neuromodulation therapy and avoidance regions of the vessel less suitable for neuromodulation therapy; and displaying, on a user interface, the CFD representation of the vessel including visual indicia indicating the identified target regions and the identified avoidance regions.

18. The method of example 17, further comprising:

delivering a neuromodulation catheter to the vessel of the human patient;

monitoring a location of the neuromodulation catheter within the vessel; and indicating, via the user interface, the location of the neuromodulation catheter relative to the identified target regions and the identified avoidance regions of the vessel.

19. The method of example 17 or 18, further comprising providing, via the user interface, a recommendation, made by the processor, of whether to proceed with neuromodulation therapy at the current neuromodulation catheter location within the vessel, the recommendation being based on a comparison between the current location of the neuromodulation catheter and the identified target regions and/or the identified avoidance regions of the vessel.

20. The method of any one of examples 17-19 wherein the location of the neuromodulation catheter is monitored in real-time.

21. The method of any one of examples 17-20 wherein receiving the hemodynamic data related to the vessel comprises detecting at least one of blood pressure or blood flow using a sensor disposed within the vessel.

22. The method of any one of examples 17-21 wherein identifying the avoidance regions comprises identifying portions of the vessel having low wall shear stress (WSS), high WSS, high WSS gradients, an ostium, a carina, a taper region, a calcification, a fibromuscular dysplasia, an aneurysm, a bifurcation, a region of blood flow separation, an eddy, a region of impinged blood flow, a region of turbulent blood flow, a region of secondary blood flow, or a combination thereof.

23. The method of any one of examples 17-22, further comprising applying neuromodulation energy to at least one of the identified target regions of the vessel, wherein the neuromodulation therapy comprises energy delivery, cryotherapy and/or chemical-based treatment.

24. The method of any one of examples 17-23 wherein receiving hemodynamic data related to the vessel comprises receiving at least one of a blood pressure measurement or a blood flow measurement from a sensor of the neuromodulation catheter.

25. A non-transitory computer readable memory storing instructions that, when executed by a processor of a computing device, cause the computing device to perform operations for identifying a target neuromodulation therapy region in a blood vessel, the operations comprising:
  receiving data regarding three-dimensional imaging of the vessel;
  receiving at least one of blood pressure data or blood flow data related to the vessel;
  generating a computational fluid dynamics (CFD) model of the vessel based at least in part on the vessel imaging data and the blood pressure and/or blood flow data;
  identifying target regions of the vessel suitable for neuromodulation therapy and avoidance regions of the vessel to avoid during neuromodulation therapy, the identifying being based on the CFD model of the vessel; and
  displaying, on a user interface, a representation of the vessel including visual markers indicating the identified target regions and the identified avoidance regions.

26. A system for optimizing neuromodulation therapy in a renal blood vessel of a human patient, the system comprising:
  a neuromodulation catheter including—
    an elongate shaft having a proximal portion and a distal portion, wherein the shaft is configured to locate the distal portion intravascularly at a treatment region within the vessel of a human patient;
    a neuromodulation assembly at the distal portion of the shaft; and
    at least one sensor at the distal portion of the shaft, wherein the sensor is configured to transmit hemodynamic data regarding the blood vessel;
  a computing device having a memory and a processor, wherein the memory stores instructions that, when executed by the processor, cause the system to perform operations comprising—
    receiving digital data regarding three-dimensional imaging of the vessel;
    receiving hemodynamic data from the sensor;
    generating, at the processor, a computational fluid dynamics (CFD) model of the vessel based at least in part on the three-dimensional imaging of the vessel and the hemodynamic data;
    identifying target regions of the vessel suitable for neuromodulation therapy and avoidance regions of the vessel less suitable for neuromodulation therapy based on the CFD model; and
    displaying a representation of the vessel including visual markers indicating the avoidance regions.

27. The system of example 26 wherein the sensor comprises at least one of a blood pressure sensor or a blood flow sensor.

28. The system of example 26 or 27 wherein the neuromodulation catheter further comprises a transmitter at the distal portion of the shaft, wherein the transmitter is configured to communicate, to a receiver, the current location of the neuromodulation assembly in the vessel.

VI. Conclusion

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. For example, where a multi-electrode or multi-element neuromodulation catheter is shown herein, a single-electrode or single-element neuromodulation catheter may be used instead. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Several implementations of the disclosed technology are described above in reference to the figures. The computing devices on which the described technology may be implemented can include one or more central processing units, memory, input devices (e.g., keyboard and pointing devices), output devices (e.g., display devices), storage devices (e.g., disk drives), and network devices (e.g., network interfaces). The memory and storage devices are computer-readable storage media that can store instructions that implement at least portions of the described technology. In addition, the data structures and message structures can be stored or transmitted via a data transmission medium, such as a signal on a communications link. Various communications links can be used, such as the Internet, a local area network, a wide area network, or a point-to-point dial-up connection. Thus, computer-readable media can comprise computer-readable storage media (e.g., "non-transitory" media) and computer-readable transmission media.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A method for evaluating a vessel for neuromodulation therapy, the method comprising:
   - receiving, at a processor, digital data regarding three-dimensional imaging of the vessel;
   - receiving, at the processor, hemodynamic data regarding the vessel;
   - generating, at the processor, a computational fluid dynamics (CFD) model of the vessel based at least in part on the imaging data and the hemodynamic data;
   - identifying, with reference to the CFD model, avoidance regions of the vessel for neuromodulation therapy, wherein the avoidance regions include regions of at least one of flow separation, eddy formation, flow impingement, low wall shear stress (WSS), or high WSS gradients; and
   - displaying, on a user interface, a representation of the vessel including visual markers indicating the identified avoidance regions.

2. The method of claim 1 wherein the vessel is a renal artery, a pulmonary artery, a hepatic artery, a coronary artery, or an aorta.

3. The method of claim 1 wherein the vessel is a main vessel, at least one branch vessel of the main vessel, or at least one accessory vessel directly coupled to the at least one branch vessel or another vessel coupled to the main vessel.

4. The method of claim 1, further comprising:
   - receiving location data from a neuromodulation catheter regarding the position of the neuromodulation catheter in the vessel; and
   - providing, via the processor, a recommendation to a user of whether to proceed with neuromodulation therapy at the device position based on the identified avoidance regions.

5. The method of claim 4 wherein providing the recommendation via the processor comprises generating a signal to the user indicative of the avoidance regions, wherein the signal includes an audio signal, a visual signal, a tactile signal, or a combination thereof.

6. The method of claim 1 wherein displaying the representation of the vessel further comprises displaying markers of target regions of the vessel for delivering neuromodulation therapy.

7. The method of claim 1 wherein displaying the representation of the vessel further comprises:
   - displaying a first portion of the vessel on the representation; and
   - displaying a second portion of the vessel on the representation, wherein the second portion corresponds to one or more avoidance regions of the vessel, and wherein the displayed first portion has a lower resolution compared to the displayed second portion.

8. The method of claim 1 wherein receiving the hemodynamic data comprises receiving data regarding blood pressure, blood flow, and/or blood impedance.

9. The method of claim 1 wherein receiving the hemodynamic data comprises receiving the hemodynamic data via a guidewire having a blood pressure sensor and/or a blood flow sensor.

10. The method of claim 1 wherein receiving the hemodynamic data comprises
    - receiving blood pressure data via an external pressure cuff and/or receiving blood flow data via magnetic resonance imaging (MM), a non-invasive ultrasound Doppler shift flow meter, or a combination thereof.

11. The method of claim 1 wherein receiving the digital data regarding three-dimensional imaging of the vessel comprises receiving data acquired using angiography, x-ray imaging, computed tomography (CT), MRI, or a combination thereof.

12. The method of claim 1 wherein receiving hemodynamic data comprises receiving blood pressure data and/or blood flow data measured at a position within a main portion the vessel having at least generally laminar flow.

13. The method of claim 1 wherein receiving hemodynamic data comprises receiving blood pressure data and/or blood flow data measured at a position within at least one branch vessel and/or at least one accessory vessel.

14. The method of claim 4 wherein providing the recommendation further comprises:
    - recommending avoiding neuromodulation therapy at one or more portions of the vessel having at least one hemodynamic parameter in the hemodynamic data that exceeds a threshold hemodynamic parameter, and thereby indicates at least one local blood flow abnormality.

15. The method of claim 1 wherein identifying avoidance regions of the vessel comprises identifying portions of the vessel at or proximate to an ostium, a carina, a taper region, a calcification, a fibromuscular dysplasia, an aneurysm, a bifurcation, or a combination thereof.

16. The method of claim 1 wherein generating the computational fluid dynamic model of the vessel comprises applying a hemodynamic parameter derived from empirical data or conglomerate data.

17. A method of optimizing neuromodulation therapy in a blood vessel of a human patient, the method comprising:
    - receiving, at a processor, digital data regarding three-dimensional imaging of the vessel;
    - receiving, at the processor, hemodynamic data related to the vessel;
    - generating, at the processor, a computational fluid dynamics (CFD) representation of the vessel based at least in part on the imaging data and the hemodynamic data, the computational fluid dynamics representation including flow parameters;
    - identifying, via the processor, target regions of the vessel suitable for neuromodulation therapy and avoidance regions of the vessel less suitable for neuromodulation therapy; and
    - displaying, on a user interface, the CFD representation of the vessel including visual indicia designating the identified target regions and the identified avoidance regions.

18. The method of claim 17, further comprising:
    - delivering a neuromodulation catheter to the vessel of the human patient;
    - monitoring the location of the neuromodulation catheter within the vessel; and
    - indicating, via the user interface, the location of the neuromodulation catheter relative to the identified target regions and the identified avoidance regions of the vessel.

19. The method of claim 18, further comprising providing, via the user interface, a recommendation, made by the processor, of whether to proceed with neuromodulation therapy at the current neuromodulation catheter location within the vessel, the recommendation being based on a comparison between the current location of the neuromodulation catheter and the identified target regions and/or the identified avoidance regions of the vessel.

20. The method of claim 18 wherein the location of the neuromodulation catheter is monitored in real-time.

21. The method of claim 17 wherein receiving the hemodynamic data related to the vessel comprises detecting at least one of blood pressure or blood flow using a sensor disposed within the vessel.

22. The method of claim 17 wherein identifying the avoidance regions comprises identifying portions of the vessel having low wall shear stress (WSS), high WSS, high WSS gradients, an ostium, a carina, a taper region, a calcification, a fibromuscular dysplasia, an aneurysm, a bifurcation, a region of blood flow separation, an eddy, a region of impinged blood flow, a region of turbulent blood flow, a region of secondary blood flow, or a combination thereof.

23. The method of claim 17, further comprising applying neuromodulation therapy to at least one of the identified target regions of the vessel, wherein the neuromodulation therapy comprises energy delivery, cryotherapy, and/or chemical-based treatment.

24. The method of claim 21 wherein the sensor disposed within the blood vessel is a sensor of the neuromodulation catheter.

25. A non-transitory computer readable memory storing instructions that, when executed by a processor of a computing device, cause the computing device to perform operations for identifying a target neuromodulation therapy region in a blood vessel, the operations comprising:
  receiving data regarding three-dimensional imaging of the vessel;
  receiving at least one of blood pressure data or blood flow data related to the vessel;
  generating a computational fluid dynamics (CFD) model of the vessel based at least in part on the vessel imaging data and the blood pressure and/or blood flow data;
  identifying target regions of the vessel suitable for neuromodulation therapy and avoidance regions of the vessel to avoid during neuromodulation therapy, the identifying being based on the CFD model of the vessel; and
  displaying, on a user interface, a representation of the vessel including visual markers indicating the identified target regions and/or the identified avoidance regions.

26. A system for optimizing neuromodulation therapy in a renal blood vessel of a human patient, the system comprising:
  a neuromodulation catheter including—
    an elongate shaft having a proximal portion and a distal portion, wherein the shaft is configured to locate the distal portion intravascularly at a treatment region within the vessel of a human patient;
    a neuromodulation assembly at the distal portion of the shaft; and
    at least one sensor at the distal portion of the shaft, wherein the sensor is configured to transmit hemodynamic data regarding the blood vessel;
  a computing device having a memory and a processor, wherein the memory stores instructions that, when executed by the processor, cause the system to perform operations comprising—
    receiving digital data regarding three-dimensional imaging of the vessel;
    receiving hemodynamic data from the sensor;
    generating, at the processor, a computational fluid dynamics (CFD) model of the vessel based at least in part on the three-dimensional imaging data and the hemodynamic data;
    identifying target regions of the vessel suitable for neuromodulation therapy and avoidance regions of the vessel less suitable for neuromodulation therapy based on the CFD model; and
    displaying a representation of the vessel including visual markers indicating the avoidance regions.

27. The system of claim 26 wherein the sensor comprises at least one of a blood pressure sensor or a blood flow sensor.

28. The system of claim 26 wherein the neuromodulation catheter further comprises a transmitter at the distal portion of the shaft, wherein the transmitter is configured to communicate, to a receiver, the current location of the neuromodulation assembly in the vessel.

* * * * *